US008940874B2

(12) United States Patent
Veldman et al.

(10) Patent No.: US 8,940,874 B2
(45) Date of Patent: *Jan. 27, 2015

(54) NEUTRALIZING ANTIBODIES AGAINST GDF-8 AND USES THEREFOR

(71) Applicants: Wyeth LLC, Madison, NJ (US); MedImmune Limited, Cambridge (GB)

(72) Inventors: Geertruida M. Veldman, Sudbury, MA (US); Monique V. Davies, Harpswell, MA (US); Kening Song, Arlington, MA (US); Neil M. Wolfman, Dover, MA (US); Kristie Grove Bridges, Maynard, MA (US); Anne Field, Royston (GB); Caroline Russell, Royston (GB); Viia Valge-Archer, Little Abington (GB)

(73) Assignees: Wyeth LLC, Wilmington, DE (US); MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/691,395

(22) Filed: Nov. 30, 2012

(65) Prior Publication Data

US 2013/0287762 A1 Oct. 31, 2013

Related U.S. Application Data

(62) Division of application No. 12/632,383, filed on Dec. 7, 2009, now Pat. No. 8,420,082, which is a division of application No. 11/777,525, filed on Jul. 13, 2007, now Pat. No. 7,655,763, which is a division of application No. 10/688,925, filed on Oct. 21, 2003, now Pat. No. 7,261,893.

(60) Provisional application No. 60/419,964, filed on Oct. 22, 2002.

(51) Int. Cl.
| | |
|---|---|
| *C07K 16/00* | (2006.01) |
| *C07K 16/18* | (2006.01) |
| *C07K 16/22* | (2006.01) |
| *A61K 39/00* | (2006.01) |
| *A61K 39/395* | (2006.01) |

(52) U.S. Cl.
CPC ........... *C07K 16/22* (2013.01); *A61K 2039/505* (2013.01); *C07K 2317/622* (2013.01); *C07K 2317/21* (2013.01)
USPC ........... 530/388.23; 530/387.1; 530/387.9; 530/388.1; 530/387.3; 530/388.24; 424/133.1; 424/135.1; 424/139.1; 424/141.1; 424/142.1; 424/145.1; 424/158.1

(58) Field of Classification Search
None
See application file for complete search history.

(56) References Cited

U.S. PATENT DOCUMENTS

| | | | |
|---|---|---|---|
| 5,639,638 A | 6/1997 | Wozney et al. | |
| 5,700,911 A | 12/1997 | Wozney et al. | |
| 5,723,125 A | 3/1998 | Chang et al. | |
| 5,756,457 A | 5/1998 | Wang et al. | |
| 5,824,307 A | 10/1998 | Johnson | |
| 5,827,733 A | 10/1998 | Lee et al. | |
| 5,914,234 A | 6/1999 | Lee et al. | |
| 5,994,618 A | 11/1999 | Lee et al. | |
| 6,004,937 A | 12/1999 | Wood et al. | |
| 6,096,506 A | 8/2000 | Lee et al. | |
| 6,340,668 B1 | 1/2002 | Celeste et al. | |
| 6,368,597 B1 | 4/2002 | Strassmann et al. | |
| 6,369,201 B1 | 4/2002 | Barker et al. | |
| 6,407,213 B1 | 6/2002 | Carter et al. | |
| 6,437,111 B1 | 8/2002 | Wozney et al. | |
| 6,465,239 B1 | 10/2002 | Lee et al. | |
| 6,607,884 B1 | 8/2003 | Lee et al. | |
| 6,656,475 B1 | 12/2003 | Lee et al. | |
| 6,673,534 B1 | 1/2004 | Lee et al. | |
| 6,696,260 B1 | 2/2004 | Lee et al. | |
| 6,835,544 B2 | 12/2004 | Mathews et al. | |
| 6,891,082 B2 | 5/2005 | Lee et al. | |
| 7,101,551 B2 | 9/2006 | Itami et al. | |
| 7,192,717 B2 | 3/2007 | Hill et al. | |
| 7,261,893 B2 | 8/2007 | Veldman et al. | |
| 7,320,789 B2 | 1/2008 | Aghajanian et al. | |
| 7,381,528 B2 | 6/2008 | Lee et al. | |
| 7,393,682 B1 | 7/2008 | Lee et al. | |
| 7,655,763 B2 * | 2/2010 | Veldman et al. | ......... 530/388.23 |
| 8,420,082 B2 | 4/2013 | Veldman et al. | |
| 2002/0127234 A1 | 9/2002 | El Halawani et al. | |
| 2002/0150577 A1 | 10/2002 | Lee et al. | |
| 2002/0157125 A1 | 10/2002 | Lee et al. | |

(Continued)

FOREIGN PATENT DOCUMENTS

| | | |
|---|---|---|
| EP | 1 013 762 | 6/2000 |
| EP | 1 061 940 B1 | 12/2003 |

(Continued)

OTHER PUBLICATIONS

Alexander et al., "Human Parathyroid Hormone 1-34 Reverses Bone Loss in Ovariectomized Mice", *J. Bone Min. Res.*, 16:1665-1673 (2001).

Alliel et al., "Testican, a Multidomain Testicular Proteoglycan Resembling Modulators of Cell Social Behaviour", *Eur. J. Biochem.*, 214:347-350 (1993).

Amthor et al., "The Expression and Regulation of Follistatin and a Follistatin-like Gene During Avian Somite Compartmentalization and Myogenesis", *Dev. Biol.*, 178:343-362 (1996).

Andersson et al., "Repeated In Vivo Determinations of Bone Mineral Density During Parathyroid Hormone Treatment in Ovariectomized Mice", *J. Endocrinol.*, 170:529-537 (2001).

(Continued)

*Primary Examiner* — Elizabeth C Kemmerer
(74) *Attorney, Agent, or Firm* — DLA Piper LLP (US)

(57) ABSTRACT

The disclosure provides novel antibodies against growth and differentiation factor-8 (GDF-8), in particular human antibodies, and antibody fragments, including those that inhibit GDF-8 activity in vitro and/or in vivo. The disclosure also provides methods for diagnosing, preventing, or treating degenerative disorders of muscle or bone, or disorders of insulin metabolism.

12 Claims, 18 Drawing Sheets

(56) References Cited

U.S. PATENT DOCUMENTS

| | | |
|---|---|---|
| 2003/0074680 A1 | 4/2003 | Lee et al. |
| 2003/0104406 A1 | 6/2003 | Wolfman et al. |
| 2003/0138422 A1 | 7/2003 | Aghajanian et al. |
| 2003/0162714 A1 | 8/2003 | Hill et al. |
| 2003/0180306 A1 | 9/2003 | Hill et al. |
| 2004/0055027 A1 | 3/2004 | Lee et al. |
| 2004/0077053 A1 | 4/2004 | Lee et al. |
| 2004/0138118 A1 | 7/2004 | Wolfman et al. |
| 2004/0181033 A1 | 9/2004 | Han et al. |
| 2004/0223966 A1 | 11/2004 | Wolfman et al. |
| 2005/0043232 A1 | 2/2005 | Lee et al. |
| 2005/0257278 A1 | 11/2005 | Lee et al. |
| 2006/0240487 A1 | 10/2006 | Nowak et al. |
| 2006/0240488 A1 | 10/2006 | Nowak et al. |
| 2008/0178310 A1 | 7/2008 | Lee et al. |
| 2008/0213426 A1 | 9/2008 | Lee et al. |

FOREIGN PATENT DOCUMENTS

| | | |
|---|---|---|
| EP | 1 444 985 A2 | 8/2004 |
| WO | WO 94/21681 | 9/1994 |
| WO | WO 94/26892 | 11/1994 |
| WO | WO 96/01845 | 1/1996 |
| WO | WO 98/33887 | 8/1998 |
| WO | WO 98/35019 | 8/1998 |
| WO | WO 99/02667 | 1/1999 |
| WO | WO 99/06559 | 2/1999 |
| WO | WO 99/24058 | 5/1999 |
| WO | WO 99/24618 | 5/1999 |
| WO | WO 99/40181 | 8/1999 |
| WO | WO 99/45949 | 9/1999 |
| WO | WO 99/56768 | 11/1999 |
| WO | WO 00/11163 | 3/2000 |
| WO | WO 00/43781 | 7/2000 |
| WO | WO 01/05820 | 1/2001 |
| WO | WO 01/58956 | 8/2001 |
| WO | WO 01/64888 | 9/2001 |
| WO | WO 01/90190 | 11/2001 |
| WO | WO 02/09641 | 2/2002 |
| WO | WO 02/068650 | 9/2002 |
| WO | WO 03/027248 | 4/2003 |
| WO | WO 03/037248 | 5/2003 |
| WO | WO 03/072714 | 9/2003 |
| WO | WO 03/072715 | 9/2003 |
| WO | WO 2004/039948 | 5/2004 |
| WO | WO 2004/108157 | 12/2004 |
| WO | WO 2006/102574 | 9/2006 |
| WO | WO 2006/107611 | 10/2006 |

OTHER PUBLICATIONS

Ashmore et al., "Comparative Aspects of Muscle Fiber Types in Fetuses of the Normal and Double-Muscled' Cattle", *Growth*, 38:501-506 (1974).

Attisano et al., "Activation of Signalling by the Activin Receptor Complex", *Mol. Cell. Biol.*, 16:1066-1073 (1996).

Bakker et al., "Duchenne and Becker Muscular Dystrophies. In Diagnostic Criteria for Neuromuscular Disorders", 2nd ed., Emery, ed., *Royal Society of Medicine Press*, 1998; pp. 1-4.

Bartholin et al., "FLRG, an Activin-Binding Protein, is a New Target of TGFp Transcription Activation Through Smad Proteins", *Oncogene*, 20:5409-5419 (2001).

Bellinge et al., "Myostatin and Its Implications on animal breeding: a review", *Animal Genetics*, 36:1-6 (2005).

Bogdanovich et al., "Functional Improvement of Dystrophic Muscle by Myostatin Blockade", *Nature*, 420:418-421 (2002).

Bork et al., "Go hunting in sequence databases but watch out for the traps" Trends in *Genetics*, 12:425-427 (1996).

Bork, "Powers and Pitfalls in Sequence Analysis: the 70% Hurdle", *Genome Research*, 10:398-400 (2000).

Brenner, "Errors in genome annotation", *Trends in Genetics*, 15:132-133 (1999).

Brown et al., "Physicochemical Activation of Recombinant Latent Transforming Growth Factor-beta's 1,2, and 3", *Growth Factors*, 3:35-43 (1990).

Bulfield et al., "X Chromosome-Linked Muscular Dystrophy (mdx) in the Mouse", *Proc. Natl. Acad. Sci. U.S.A.*, 81:1189-1192 (1984).

Casas et al., "Association of the Muscle Hypertrophy Locus with Carcass Traits in Beef Cattle", *J. Anim. Sci.*, 76:468-473 (1998).

Cohn et al., "Myostatin does not regulate cardiac hypertrophy or fibrosis", *Neuromuscular Disorders*, 17:290-296 (2007).

D'Angelo et al., "Authentic Matrix Vesicles Contain Active Metalloproteases (MMP)", *J. Biol. Chem.*, 276:11347-11353 (2001).

Derynck et al., "Human Transforming Growth Factor-13 Complementary DNA Sequence and Expression in Normal and Transformed Cells", *Nature*, 316:701-705 (1985).

Dickman, Steven, "Gene Mutation Provides More Meat on the Hoof", *Science*, 277:1922-1923 (1997).

Doerks et al., "Protein annotation: detective work for function prediction", *Trends in Genetics*, 14:248-250 (1998).

Donoghue et al., "Rostrocaudal Gradient of Transgene Expression in Adult Skeletal Muscle", *Proc. Natl. Acad. Sci.*, U.S.A. 88:5847-5851 (1991).

Emery, "The Muscular Dystrophies", *Lancet*, 359:687-695 (2002).

Escolar et al., "Pharmacologic and Genetic Therapy for Childhood Muscular Dystrophies", *Current Neurology and Neuroscience Reports*, 1:168-174 (2001).

Gamer et al., "A Novel BMP Expressed in Developing Mouse Limb, Spinal Cord, and Tail Bud Is a Potent Mesoderm Inducer in Xenopus Embryos", *Dev. Biol.*, 208:222-232 (1999).

Gamer et al., "Gdf11 is a Negative Regulator of Chondrogenesis and Myogenesis in the Developing Chick Limb", *Dev. Biol.*, 229:407-420 (2001).

Gentry et al., "The Pro Domain of Pre-Pro-Transforming Growth Factor (31 When Independently Expressed Is a Functional Binding Protein for the Mature Growth Factor", *Biochemistry*, 29:6851-6857 (1990).

Gillis, "Multivariate Evaluation of the Functional Recovery Obtained by the Overexpression of Utrophin in Skeletal Muscles of the mdx Mouse", *Neuromuscular Disorders*, 12:S90-S94 (2002).

Gonzalez-Cadavid et al., "Organization of the Human Myostatin Gene and Expression in Healthy Men and HIV-Infected Men With Muscle Wasting", *PNAS*, 95:14938-14943 (1998).

Grady et al., "Skeletal and Cardiac Myopathies in Mice Lacking Utrophin and Dystrophin: A Model for Duchenne Muscular Dystrophy", *Cell*, 90:729-738 (1997).

Granchelli et al., "Pre-Clinical Screening of Drugs Using the mdx Mouse", *Neuromuscular Disorders*, 10:235-239 (2000).

Grobet et al., "A Deletion in the Bovine Myostatin Gene Causes the Double-Muscled Phenotype in Cattle", *Nature Genetics*, 17:71-74 (1997).

Hamrick et al., "Bone Mineral Content and Density in the Humerus of Adult Myostatin-Deficient Mice", *Calcif. Tissue Int.*, 71(1):63-68 (2002).

Hamrick et al., "Femoral Morphology and Cross-Sectional Geometry of Adult Myostatin-Deficient Mice", *Bone*, 27:343-349 (2000).

Hayette et al., "FLRG (Follistatin-Related Gene), A New Target of Chromosomal Rearrangement in Malignant Blood Disorders", *Oncogene*, 16:2949-2954 (1998).

Hill et al., "Regulation of Myostatin in Vivo by Growth and Differentiation Factor-Associated Serum Protein-1: A Novel Protein with Protease Inhibitor and Follistatin Domains", *Mol. Endocrinol.*, 17:1144-1154 (2003).

Hill et al., "The Myostatin Propeptide and the Follistatin-Related Gene Are Inhibitory Binding Proteins of Myostatin in Normal Serum", *J. Biol. Chem.*, 277:40735-40741 (2002).

Hoffman et al., "Conservation of the Duchenne Muscular Dystrophy Gene in Mice and Humans", *Science*, 238:347-350 (1987).

Hoodless et al., "Mechanisms and Function of Signaling by the TGFβ Superfamily", *Current Topics in Microbiology and Immunology*, pp. 236-272 (1998).

Huet et al., "Skeletal Muscle Cell Hypertrophy Induced by Inhibitors of Metalloproteases; Myostatin as a Potential Mediator", *Am. J. Physio. Cell. Physiol.*, 281:C1624-C1634(2001).

Jiang et al., "Characterization and Identification of the Inhibitory Domain of GDF-8 Propeptide", *Biochem. Biophys. Res. Commun.*, 315:525-531 (2004).

(56) References Cited

OTHER PUBLICATIONS

Kambadur et al., "Mutations in Myostatin (GDF8) in Double-Muscled Belgian Blue and Piedmontese Cattle", *Genome Res.*, 7:910-915 (1997).
Kato, "A Secreted Tumor-Suppressor, mac25, with Activin-Binding Activity", *Mol. Med.*, 8:126-135(2000).
Kessler et al., "Bone Morphogenetic Protein-1: The Type I Procollagen C-Proteinase", *Science*, 271:360-362 (1996).
Khurana et al., "Pharmacological Strategies for Muscular Dystrophy", *Nature Rev. Drug Disc.*, 2:379-386 (2003).
Kim et al., "Inhibition of Preadipocyte Differentiation by Myostatin Treatment in 3T3-L1 Cultures", *Biochem. Biophys. Res. Comm.*, 281:902-906 (2001).
Kingsley, D.M. "The TGF-β Superfamily: New Members, New Receptors, and New Genetic Tests of Function in Different Organisms", *Genes & Devel.*, 8:133-146 (1994).
Lang et al., "Regulation of Myostatin by Glucocorticoids After Thermal Injury", *FASEB J.*, 15:1807-1809 (2001).
Lee et al., "Analysis of Site-Directed Mutations in Human Pro-a2(I) Collagen Which Block Cleavage by the C-Proteinase", *J. Biol Chem.*, 265:21992-21996 (1990).
Lee et al., "Regulation of Myostatin Activity and Muscle Growth", *PNAS*, 98:9306-9311 (2001).
Li et al., "The C-Proteinase that Processes Procollagens to Fibrillar Collagens is Identical to the Protein Previously Identified as Bone Morphogenic Protein-1", *Proc. Natl. Acad. Sci. U.S.A.*, 93:5127-5130 (1996).
Lin et al., "Expression Cloning of the TGF-β Type II Receptor, a Functional Transmembrane Serine/Threonine Kinase", *Cell*, 68:775-785 (1992).
Liu et al., "Assigning the Positional Identity of Spinal Motor Neurons: Rostrocaudal Patterning of Hox-c Expression by FGFs, Gdf11, and Retinoids", *Neuron*, 32:997-1012 (2001).
Lyons et al., "Proteolytic Activation of Latent Transforming Growth Factor-β from Fibroblast-Conditioned Medium", *J. Cell Biol.*, 106:1659-1665 (1988).
Maeda et al., "Activation of Latent Transforming Growth Factor β1 by Stromelysin 1 in Extracts of Growth Plate Chondrocyte-Derived Matrix Vesicles", *J. Bone Miner. Res.*, 16:1281-1290 (2001).
Maguer-Satta et al., "During Hematopoiesis, Expression of FLRG, a Novel Activin A Ligand, is regulated by TGF-β", *Exp. Hematol.*, 29:301-308 (2001).
Marques et al., "Production of a DPP Activity Gradient in the Early Drosophilia Embryo through the Opposing Actions of the SOG and TLD Proteins", *Cell*, 91:417-426 (1997).
Massagué et al., "Receptors for the TGF-β Family", *Cell*, 69:1067-1070 (1992).
Massagué et al., "The TGF-β Family and its Composite Receptors", *Trends Cell Biol.*, 4:172-178 (1994).
Massagué, "How Cells Read TGF-β Signals", *Nature Rev. Mol. Cell. Biol.*, 1:169-178 (2000).
Massagué, J., "The Transforming Growth Factor-β Family", *Ann. Rev. Cell Biol.*, 6:597-641 (1990).
Matsuda et al., "Visualization of Dystrophic Muscle Fibers in Mdx Mouse by Vital Staining with Evans Blue: Evidence of Apoptosis in Dystrophin-Deficient Muscle", *J. Biochem.*, 118:959-964 (1995).
McKnight, Steven L., "Gatekeepers of Organ Growth", *Proc. Natl. Acad. Sci. USA*, 94:12249-12250 (1997).
McPherron et al., "Double Muscling in Cattle Due to Mutations in the Myostatin Gene", *PNAS*, 94:12457-12461 (1997).
McPherron et al., "Regulation of Anterior/Posterior Patterning of the Axial Skeleton by Growth/Differentiation Factor 11", *Nature Genet.*, 22:260-264 (1999).
McPherron et al., "Regulation of Skeletal Muscle Mass in Mice by a New TGF-β Superfamily Member", *Nature*, 387:83-90 (1997).
McPherron et al., "Suppression of Body Fat Accumulation in Myostatin-Deficient Mice", *J. Clin. Invest.*, 109:595-601 (2002).
Mennissier, F., "Present State of Knowledge About the Genetic Determination of Muscular Hypertrophy or the Double Muscled Trait in Cattle", *Muscle Hypertrophy of Genetic Origin and Its Uses to Improve Beef Production: A Seminar in CEC Programme of Coordinated Research on Beef Production* :387-428 (1982).
Miyazono et al., "Latent High Molecular Weight Complex of Transforming Growth Factor β1", *J. Biol. Chem.*, 263:6407-6415 (1988).
Morrison et al., "T-Cell-Dependent Fibrosis in the mdx Dystrophic Mouse", *Lab. Invest.*, 80:881-891 (2000).
Motamed, "Moleclues in Focus, SPARC (Osteonectin/BM-40)", *Int. J. Biochem. Cell Biol.*, 31:1363-1366 (1999).
Moustakas et al., "Smad Regulation in TGF-β Signal Transduction", *J. Cell Sci.*, 114:4359-4369 (2001).
Murphy et al., "Acute antibody-directed myostatin inhibition attenuates disuse muscle atrophy and weakness in mice", *J. Appl. Physiol.*, 110:1065-1072 (2011).
Muyldermans et al., "Recognition of antigens by single-domain antibody fragments: the superfluous luxury of paired domains", *Trends Biochem. Sci.*, 26:230-35 (2001).
Nakamura et al., "Follistatin, an Activin-Binding Protein, Associates with Heparan Sulfate Chains of Proteoglycans on Follicular Granulosa Cells", *J. Biol. Chem.*, 266:19432-19437 (1991).
Nakamura et al., "Isolation and Characterization of Activin Receptor from Mouse Embryonal Carcinoma Cells", *J. Biol. Chem.*, 267:18924-18928 (1992).
Nakashima et al., "Expression of Growth/Differentiation Factor 11, A New Member of the BMP/TGF β Superfamily During Mouse Embryogenesis", *Mech. Dev.*, 80:185-189 (1999).
Ngo et al., *In the Protein Folding Problems and Tertiary Structure Prediction*, Merz et al., eds., Brickhauser, Springer Verlag, Boston, pp. 433-434 & 492-495 (1994).
Pappano et al., "Use of BMP1-T111 Doubly Homozygous Null Mice and Proteomics to Identify and Validate In Vivo Substrates of Bone Morphogenetic Protein 1/Tolloid-Like Metalloproteinases", *Mol. Cell. Biol.*, 23:4428-4438 (2003).
Patel et al., "Cloning and Early Dorsal Axial Expression of Flik, a Chick Follistatin-Related Gene: Evidence for Involvement in Dorsalization-Neural Induction", *Dev. Biol.*, 178: 327-342 (1996).
Patthy et al., "Functions of Agrin and Agrin-Related Proteins", *Trends Neurosci.*, 16:76-81 (1993).
Phillips et al., "Follistatin: A Multifunctional Regulatory Protein", *Front. Neuroendocrin.*, 19:287-322 (1998).
Piccolo et al., "Cleavage of Chordin by Xolloid Metalloprotease Suggests a Role for Proteolytic Processing in the Regulation of Spemann Organizer Activity", *Cell*, 91:407-416 (1997).
Queen et al. "A humanized antibody that binds to the interleukin 2 receptor", *PNAS USA*, 86:10029-10033 (1989).
R&D Systems, Inc., "Recombinant Human Activin Receptor IIB-Fc Chimera: Specifications and Use", Cat. No. 339-RB (2002).
Riley et al., "The Use of Single Nucleotide Polymorphisms in the Isolation of Common Disease Genes", *Pharmacogenomics*, 1:39-47 (2000).
Sato et al., "Inhibition of Endothelial Cell Movement by Pericytes and Smooth Muscle Cells: Activation of a Latent Transforming Growth Factor-β1-Like Molecule by Plasmin During Co-Culture", *J. Cell Biol.*, 109:309-315 (1989).
Schacke et al., "Mechanisms Involved in the Side Effects of Glucocorticoids", *Pharmacol. Ther.*, 96:23-43 (2002).
Schneyer et al., "Follistatin-Related Protein (FSRP): A New Member of the Follistatin Gene Family", *Mol. Cell. Endocrinol.*, 180:33-38 (2001).
Scott et al., "Bone Morphogenetic Protein-1 Processes Probiglycan", *J. Biol. Chem.*, 275:30504-30511 (2000).
Scott et al., "Mammalian BMP-1-Tolloid-Related Metalloproteinases, Including Novel Family Member Mammalian Tolloid-Like 2, Have Differential Enzymatic Activities and Distributions of Expression Relevant to Patterning and Skeletogenesis", *Dev. Biol.*, 213:283-300 (1999).
Shibanuma et al., "Cloning From a Mouse Osteoblastic Cell Line of a Set of Transforming-Growth-Factor-β1-Regulated Genes, One of Which Seems to Encode a Follistatin-Related Polypeptide", *Eur. J. Biochem.*, 217:13-19 (1993).
Skolnick et al., "From genes to protein structure and function: novel applications of computational approaches in the genomic era", *Trends in Biotech.*, 18(1):34-39 (2000).

(56) References Cited

OTHER PUBLICATIONS

Smith et al., "The challenges og genome sequence annotation of 'The devil is in the details'", *Nature Biotechnology*, 15:1222-1223 (1997).
Sternberg et al., "Identification of Upstream and Intragenic Regulatory Elements that Confer Cell-Type-Restricted and Differentiation-Specific Expression on the Muscle Creatine Kinase Gene", *Mol. Cell. Biol.*, 8:2896-2909 (1988).
Swatland et al., "Fetal Development of the Double Muscled Condition in Cattle", *J. Animal Sci.*, 38 :752-757 (1974).
Takahara et al., "Bone Morphogenetic Protein-1 and a Mammalian Tolloid Homologue (mTld) Are Encoded by Alternatively Spliced Transcripts Which Are Differentially Expressed in Some Tissues", *J. Biol. Chem.*, 269:32572-32578 (1994).
Takahara et al., "Characterization of a Novel Gene Product (Mammalian Tolloid-like) with High Sequence Similarity to Mammalian Tolloid/Bone Morphogenetic Protein-1", *Genomics*, 34:157-165 (1996).
Thies et al., "GDF-8 Propeptide Binds to GDF-8 and Antagonizes Biological Activity by Inhibiting GDF-8 Receptor Binding", *Growth Factors*, 18:251-259 (2001).
Torres et al., "The Mutant mdx: Inherited Myopathy in the Mouse", *Brain*, 110:269-299 (1987).
Trexler et al., "A Human Protein Containing Multiple Types of Protease-Inhibitory Modules", *Proc. Natl. Acad. Sci. U.S.A.*, 98:3705-3709 (2001).
Trexler et al., "Distinct Expression Pattern of Two Related Human Proteins Containing Multiple Types of Protease-Inhibitory Modules", *Biol. Chem.*, 383:223-228 (2002).
Tsuchida et al., "Identification and Characterization of a Novel Follistatin-like Protein as a Binding Protein for the TGF-β Family", *J. Biol. Chem.*, 275:40788-40796 (2000).
Tsuchida et al., "Intracellular and Extracellular Control of Activin Function by Novel Regulatory Molecules", *Mol. Cell. Endocrinol.*, 180:25-31 (2001).
Umland et al., "Review of the Molecular and Cellular Mechanisms of Action of Glucocorticoids for Use in Asthma", *Pulmonary Pharmacology & Therapeutics*, 15:35-50 (2002).
Uzel et al., "Multiple Bone Morphogenetic Protein 1-Related Mammalian Metalloproteinases Process Pro-Lysyl Oxidase at the Correct Physiological Site and Control Lysyl Oxidase Activation in Mouse Embryo Fibroblast Cultures", *J. Biol. Chem.*, 276:22537-22543 (2001).
van der Beucken et al., "Building Novel Binding Ligands to B7.1 and B7.2 Based on Human Antibody Single Variable Light Chain Domains", *J. Mol. Bio.*, 310:591-601 (2001).
Vukicevic et al., "Induction of nephrogenic mesenchyme by osteogenic protein 1 (bone morphogenetic protein 7)", *Proc. Natl. Acad. Sci. U.S.A.*, 93:9021-9026 (1996).
Wagner et al., "Loss of Myostatin Attenuates Severity of Muscular Dystrophy in mdx Mice", *Ann. Neurol.*, 52:832-836 (2002).
Wakefield et al., "Latent Transforming Growth Factor-β From Human Platelets", *J. Biol. Chem.*, 263:7646-7654 (1988).
Ward et al., "Binding activities of a repertoire of single immunoglobulin variable domains secreted from *Escherichia coli*", *Nature*, 341:544-546 (1989).
Wells, "Additivity of Mutational Effects in Proteins", *Biochemistry*, 29:8509-8517 (1990).
Whittemore et al., "Inhibition of Myostatin in Adult Mice Increases Skeletal Muscle Mass and Strength", *Biochem. Biophys. Res. Comm.*, 300:965-971 (2003).
Wolfman et al., "Activation of Latent Myostatin by the BMP-1/Tolloid Family of Metalloproteinases", *Proc. Natl. Acad. Sci. U.S.A.*, 100:15842-15846 (2003).
Wu et al., "Autoregulation of Neurogenesis by GDF-11", *Neuron*, 37:197-207 (2003).
Wuytens et al., "Identification of Two Amino Acids in Activin A That Are Important for Biological Activity and Binding to the Activin Type II Receptors", *J. Biol. Chem.*, 274:9821-9827 (1999).
Yu et al., "Cell Surface-Localized Matrix Metalloproteinase-9 Proteolytically Activates TGF-β and Promotes Tumor Invasion and Angiogenesis", *Genes Dev.*, 14:163-176 (2000).
Zhang et al., "Inhibition of myostatin protects against diet-induced obesity by enhancing fatty acid oxidation and promoting a brown adipose phenotype in mice", *Diabetologia*, 55:183-193 (2012).
Zhu et al., "Dominant Negative Myostatin Produces Hypertrophy without Hyperplasia in Muscle", *FEBS Lett.*, 474:71-75 (2000).
Zimmers et al., "Induction of Cachexia in Mice by Systematically Administered Myostatin", *Science*, 296:1486-1488 (2002).
Zwusen et al., "Characterization of a Rat $C_6$ Glioma-Secreted Follistatin-Related Protein (FRP) Cloning and Sequence of the Human Homologue", *Eur. J. Biochem.*, 225:937-946 (1994).

* cited by examiner

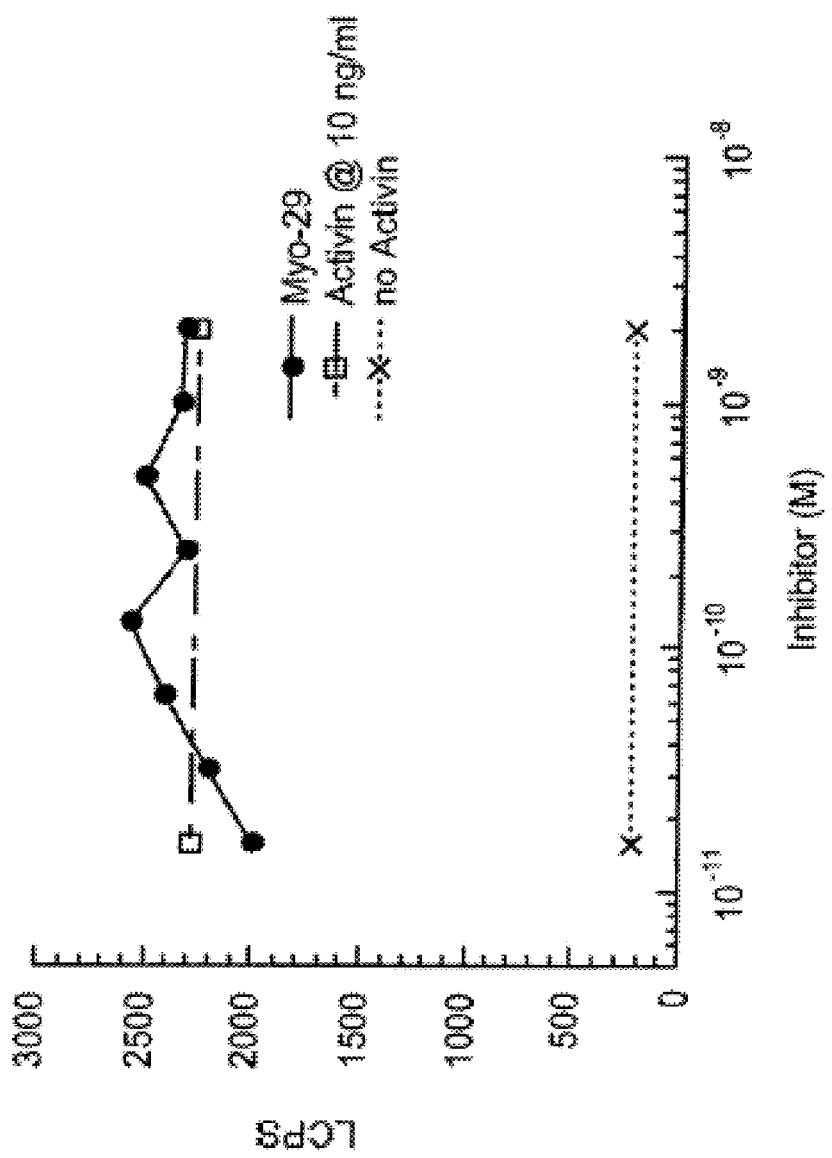

SEQUENCE LISTING

```
<160> NUMBER OF SEQ ID NOS: 54

<210> SEQ ID NO 1
<211> LENGTH: 786
<212> TYPE: DNA
<213> ORGANISM: Homo sapiens

<400> SEQUENCE: 1
gaggtgcagc tgttggagtc tgggggaggc ttggtacagc ctgggggtc cctgagactc      60
```

```
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtga gagaatgggg    300
ccctgtactg gtggaagctg ctacgacacc cttggcaact ggggccgggg caccctggtc    360
accgtctcga gtggaggcgg cggttcaggc ggaggtggct ctggcggtgg cggaagtgca    420
cagtctgtgc tgacgcagcc gccctcagtg tctggggccc agggcagag ggtcaccatc     480 tcctgcactg ggagcagctc caacatcggg gcaggttatg atgtacactg gtaccagcaa    540
cttccaggcg cggcccccaa actcctcatc agggtaatg gcaatcggcc ctcagggggtc    600 cctgaccgat tctctgtctc caagtctggc tactcagcct ccctggccat cactgggctg    660
cagcctgccg atgagggtgt ttattactgc agtcctatg acagcagtct gagtggttcg     720
aaggtgttcg gccaagggac caagctgacc gtcctaggtg cggccgcaca tcatcatcac    780
catcac                                                               786

<210> SEQ ID NO 2
<211> LENGTH: 262
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Glu Arg Met Gly Pro Cys Thr Gly Gly Ser Cys Tyr Asp Thr Leu Gly
            100                 105                 110

Asn Trp Gly Arg Gly Thr Leu Val Thr Val Ser Ser Gly Gly Gly Gly
        115                 120                 125

Ser Gly Gly Gly Gly Ser Gly Gly Gly Gly Ser Ala Gln Ser Val Leu
    130                 135                 140

Thr Gln Pro Pro Ser Val Ser Gly Ala Pro Gly Gln Arg Val Thr Ile
145                 150                 155                 160

Ser Cys Thr Gly Ser Ser Ser Asn Ile Gly Ala Gly Tyr Asp Val His
                165                 170                 175

Trp Tyr Gln Gln Leu Pro Gly Ala Ala Pro Lys Leu Leu Ile Arg Gly
            180                 185                 190

Asn Gly Asn Arg Pro Ser Gly Val Pro Asp Arg Phe Ser Val Ser Lys
        195                 200                 205

Ser Gly Tyr Ser Ala Ser Leu Ala Ile Thr Gly Leu Gln Pro Ala Asp
    210                 215                 220

Glu Gly Val Tyr Tyr Cys Gln Ser Tyr Asp Ser Ser Leu Ser Gly Ser
225                 230                 235                 240
```

```
Lys Val Phe Gly Gln Gly Thr Lys Leu Thr Val Leu Gly Ala Ala Ala
                245                 250                 255

His His His His His His
            260

<210> SEQ ID NO 3
<211> LENGTH: 372
<212> TYPE: DNA
<213> ORGANISM: Homo sapiens

<400> SEQUENCE: 3
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtga gagaatgggg     300
ccctgtactg gtgtacgacgc ctacgacacc cttggcaact ggggccgggg caccctggtc     360
accgtctcga gt                                                         372

<210> SEQ ID NO 4
<211> LENGTH: 124
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Glu Arg Met Gly Pro Cys Thr Gly Gly Ser Cys Tyr Asp Thr Leu Gly
            100                 105                 110

Asn Trp Gly Arg Gly Thr Leu Val Thr Val Ser Ser
        115                 120

<210> SEQ ID NO 5
<211> LENGTH: 336
<212> TYPE: DNA
<213> ORGANISM: Homo sapiens

<400> SEQUENCE: 5
cagtctgtgc tgacgcagcc gccctcagtg tctggggccc cagggcagag ggtcaccatc      60
tcctgcactg ggagcagctc caacatcggg gcaggttatg atgtacactg gtaccagcaa     120
cttccaggcg cggccccccaa actcctcatc agggggtaatg gcaatcggcc ctcagggggtc    180 cctgaccgat tctctgtctc caagtctggc tactcagcct ccctggccat cactgggctg     240
cagcctgccg atgagggtgt ttattactgc cagtcctatg acagcagtct gagtggttcg     300
aaggtgttcg gccaagggac caagctgacc gtccta                               336
```

<210> SEQ ID NO 6
<211> LENGTH: 112
<212> TYPE: PRT
<213> ORGANISM: Homo sapiens

<400> SEQUENCE: 6

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Ala Ala Pro Lys Leu
        35                  40                  45

Leu Ile Arg Gly Asn Gly Asn Arg Pro Ser Gly Val Pro Asp Arg Phe
    50                  55                  60

Ser Val Ser Lys Ser Gly Tyr Ser Ala Ser Leu Ala Ile Thr Gly Leu
65                  70                  75                  80

Gln Pro Ala Asp Glu Gly Val Tyr Tyr Cys Gln Ser Tyr Asp Ser Ser
                85                  90                  95

Leu Ser Gly Ser Lys Val Phe Gly Gln Gly Thr Lys Leu Thr Val Leu
            100                 105                 110

<210> SEQ ID NO 7
<211> LENGTH: 774
<212> TYPE: DNA
<213> ORGANISM: Homo sapiens

<400> SEQUENCE: 7
caggtcacct tgaaggagtc tggggggaggc ttggtacagc ctgggggggtc cctgagactc      60
tcctgtgcag cctctggatt caccttagt agatatgtca tcaactgggt ccgccaggct     120
ccagggaagg ggctggaatg ggtctcagct attagtgtta ctggtggtag cacggcctac     180
gcagactccg tgaggggccg gttcaccatc tccagagaca attccaagaa cacgctgtat     240
ttgcaaatga atagcctgag agccgaggac acggccgtat attactgtac gaaaggacag     300
tgggaacggg gaagttacta ctttgactac tggggccggg aaccctggt caccgtctcg     360
agtggaggcg gcggttcagg cggaggtggc tctggcggtg gcggaagtgc acagtctgtg     420
ctgacgcagc cgccctcagt gtctggggcc cagggcagag ggtcaccat ctcctgcact     480
gggagcagct ccaacatcgg ggacggttat gatgtacact ggtatcagca gcttccagga     540
acagccccca aactcctcat ctatggtaac agtcatcggc cctcagggggt ccctgaccga     600
ttctctggct ccaagtctga cacctctgcc tccctggcca tcactgggct ccaggttgag     660
gatgaggctg attatttctg ccactccat gacggcagtg tgagtggctg gattttcggc     720
ggagggacca agctgaccgt cctaggtgcg gccgcacatc atcatcacca tcac           774

<210> SEQ ID NO 8
<211> LENGTH: 258
<212> TYPE: PRT
<213> ORGANISM: Homo sapiens

<400> SEQUENCE: 8

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Ile Asn Trp Val Arg Gln Ala Pro Gly Lys Gly Leu Glu Trp Val

```
            35                  40                  45
Ser Ala Ile Ser Val Thr Gly Gly Thr Ala Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Gly Gln Trp Glu Arg Gly Ser Tyr Tyr Phe Asp Tyr Trp Gly
            100                 105                 110

Arg Gly Thr Leu Val Thr Val Ser Ser Gly Gly Gly Ser Gly Gly
            115                 120                 125

Gly Gly Ser Gly Gly Gly Ser Ala Gln Ser Val Leu Thr Gln Pro
        130                 135                 140

Pro Ser Val Ser Gly Ala Pro Gly Gln Arg Val Thr Ile Ser Cys Thr
145                 150                 155                 160

Gly Ser Ser Ser Asn Ile Gly Asp Gly Tyr Asp Val His Trp Tyr Gln
                165                 170                 175

Gln Leu Pro Gly Thr Ala Pro Lys Leu Leu Ile Tyr Gly Asn Ser His
            180                 185                 190

Arg Pro Ser Gly Val Pro Asp Arg Phe Ser Gly Ser Lys Ser Asp Thr
        195                 200                 205

Ser Ala Ser Leu Ala Ile Thr Gly Leu Gln Val Glu Asp Glu Ala Asp
    210                 215                 220

Tyr Phe Cys His Ser Tyr Asp Gly Ser Val Ser Gly Trp Ile Phe Gly
225                 230                 235                 240

Gly Gly Thr Lys Leu Thr Val Leu Gly Ala Ala Ala His His His
            245                 250                 255

His His

<210> SEQ ID NO 9
<211> LENGTH: 363
<212> TYPE: DNA
<213> ORGANISM: Homo sapiens

<400> SEQUENCE: 9
caggtcacct tgaaggagtc tggggggaggc ttggtacagc ctggggggtc cctgagactc     60
tcctgtgcag cctctggatt cacctttagt agatatgtca tcaactgggt ccgccaggct    120
ccagggaagg ggctggaatg ggtctcagct attagtgtta ctggtggtag cacggcctac    180
gcagactccg tgaggggccg gttcaccatc tccagagaca attccaagaa cacgctgtat    240
ttgcaaatga atagcctgag agccgaggac acggccgtat attactgtac gaaaggacag    300
tgggaacggg gaagttacta ctttgactac tggggccggg gaaccctggt caccgtctcg    360
agt                                                                   363

<210> SEQ ID NO 10
<211> LENGTH: 121
<212> TYPE: PRT
<213> ORGANISM: Homo sapiens

<400> SEQUENCE: 10

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

Val Ile Asn Trp Val Arg Gln Ala Pro Gly Lys Gly Leu Glu Trp Val
                35                  40                  45

Ser Ala Ile Ser Val Thr Gly Gly Ser Thr Ala Tyr Ala Asp Ser Val
 50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Gly Gln Trp Glu Arg Gly Ser Tyr Tyr Phe Asp Tyr Trp Gly
            100                 105                 110

Arg Gly Thr Leu Val Thr Val Ser Ser
        115                 120

<210> SEQ ID NO 11
<211> LENGTH: 336
<212> TYPE: DNA
<213> ORGANISM: Homo sapiens

<400> SEQUENCE: 11
cagtctgtgc tgacgcagcc gccctcagtg tctggggccc cagggcagag ggtcaccatc        60
tcctgcactg ggagcagctc caacatcggg gacggttatg atgtacactg gtatcagcag       120
cttccaggaa cagcccccaa actcctcatc tatggtaaca gtcatcggcc ctcaggggtc       180
cctgaccgat tctctggctc caagtctgac acctctgcct ccctggccat cactgggctc       240
caggttgagg atgaggctga ttatttctgc cactcctatg acggcagtgt gagtggctgg       300
attttcggcg agggaccaa gctgaccgtc ctaggt                                 336

<210> SEQ ID NO 12
<211> LENGTH: 111
<212> TYPE: PRT
<213> ORGANISM: Homo sapiens

<400> SEQUENCE: 12

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Asp Gly
                20                  25                  30

Tyr Asp Val His Trp Tyr Gln Gln Leu Pro Gly Thr Ala Pro Lys Leu
            35                  40                  45

Leu Ile Tyr Gly Asn Ser His Arg Pro Ser Gly Val Pro Asp Arg Phe
 50                 55                  60

Ser Gly Ser Lys Ser Asp Thr Ser Ala Ser Leu Ala Ile Thr Gly Leu
65                  70                  75                  80

Gln Val Glu Asp Glu Ala Asp Tyr Phe Cys His Ser Tyr Asp Gly Ser
                85                  90                  95

Val Ser Gly Trp Ile Phe Gly Gly Gly Thr Lys Leu Thr Val Leu
            100                 105                 110

<210> SEQ ID NO 13
<211> LENGTH: 747
<212> TYPE: DNA
<213> ORGANISM: Homo sapiens

<400> SEQUENCE: 13
caggtgcagc tggtgcaatc tggggctgag gtgaagaagc ctggggcctc agtgaaggtt        60
tcctgcaagg catctggata caccttcacc agctactata tgcactgggt gcgacaggcc       120

-continued

```
cctggacaag ggcttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagagacgag    300
aactgggggt cgaccccctg gggccaggga accctggtca ccgtctcgag tggaggcggc    360
ggttcaggcg gaggtggctc tggcggtggc ggaagtgcac tttcctatga gctgactcag    420
ccacccctca gtgtccgtgt tccaggacag acagccacca ttacctgctc tggacatgca    480
ctgggggaca aatttgtttc ctggtatcag cagggatcag gccagtcccc tgtattggtc    540
atctatgacg atacccagcg gccctcaggg atccctgggc gattctctgg ctccaactct    600
gggaacacag ccactctgac catcagcggg acccaggcta tggatgaggc tgactatttt    660
tgtcaggcgt gggacagcag cttcgtattc ggcggaggga ccaaggtcac cgtcctaggt    720
gcggccgcac atcatcatca ccatcac                                        747
```

<210> SEQ ID NO 14
<211> LENGTH: 249
<212> TYPE: PRT
<213> ORGANISM: Homo sapiens

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Glu Asn Trp Gly Phe Asp Pro Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ala Leu Ser Tyr Glu Leu Thr Gln Pro Pro Ser Val
    130                 135                 140

Ser Val Ser Pro Gly Gln Thr Ala Thr Ile Thr Cys Ser Gly His Ala
145                 150                 155                 160

Leu Gly Asp Lys Phe Val Ser Trp Tyr Gln Gln Gly Ser Gly Gln Ser
                165                 170                 175

Pro Val Leu Val Ile Tyr Asp Asp Thr Gln Arg Pro Ser Gly Ile Pro
            180                 185                 190

Gly Arg Phe Ser Gly Ser Asn Ser Gly Asn Thr Ala Thr Leu Thr Ile
        195                 200                 205

Ser Gly Thr Gln Ala Met Asp Glu Ala Asp Tyr Phe Cys Gln Ala Trp
    210                 215                 220

Asp Ser Ser Phe Val Phe Gly Gly Gly Thr Lys Val Thr Val Leu Gly
225                 230                 235                 240

Ala Ala Ala His His His His His
                245
```

<210> SEQ ID NO 15
<211> LENGTH: 351
<212> TYPE: DNA
<213> ORGANISM: Homo sapiens

<400> SEQUENCE: 15

```
caggtgcagc tggtgcaatc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccct agtggtggtag cacaagctac     180 gcacagaagt tccagggcag agtcaccatg accagggaca cgtccacgag cacagtctac     240
atggagctga gcagcctgag atctgaggac acggccgtgt attactgtgc gagagacgag     300
aactgggggt cgacccctg gggccaggga accctggtca ccgtctcgag t               351
```

<210> SEQ ID NO 16
<211> LENGTH: 117
<212> TYPE: PRT
<213> ORGANISM: Homo sapiens

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Glu Asn Trp Gly Phe Asp Pro Trp Gly Gln Gly Thr Leu
            100                 105                 110

Val Thr Val Ser Ser
        115
```

<210> SEQ ID NO 17
<211> LENGTH: 315
<212> TYPE: DNA
<213> ORGANISM: Homo sapiens

<400> SEQUENCE: 17

```
tcctatgagc tgactcagcc accctcagtg tccgtgtctc caggacagac agccaccatt      60
acctgctctg gacatgcact ggggacaaa tttgtttcct ggtatcagca gggatcaggc     120
cagtcccctg tattggtcat ctatgacgat acccagcggc cctcagggat ccctgggcga     180
ttctctggct ccaactctgg gaacacagcc actctgacca tcagcgggac ccaggctatg     240
gatgaggctg actattttg tcaggcgtgg gacagcagct cgtattcgg cggagggacc     300 aaggtcaccg tccta                                                        315
```

<210> SEQ ID NO 18
<211> LENGTH: 105
<212> TYPE: PRT
<213> ORGANISM: Homo sapiens

<400> SEQUENCE: 18

```
Ser Tyr Glu Leu Thr Gln Pro Pro Ser Val Ser Pro Gly Gln
1               5                   10                  15

Thr Ala Thr Ile Thr Cys Ser Gly His Ala Leu Gly Asp Lys Phe Val
            20                  25                  30

Ser Trp Tyr Gln Gln Gly Ser Gly Gln Ser Pro Val Leu Val Ile Tyr
        35                  40                  45

Asp Asp Thr Gln Arg Pro Ser Gly Ile Pro Gly Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Ser Phe Val Phe
                85                  90                  95

Gly Gly Gly Thr Lys Val Thr Val Leu
            100                 105

<210> SEQ ID NO 19
<211> LENGTH: 774
<212> TYPE: DNA
<213> ORGANISM: Homo sapiens

<400> SEQUENCE: 19
gaggtccagt tgttggagtc tgggggaggc ttggtacagc ctggggggtc cctgagactc      60
tcctgtgcag cctctggatt cacctttagt agatatgtca tcaactgggt ccgccaggct     120
ccagggaagg gctggaatg gtctcagct attagtgtta ctggtggtag cacggcctac      180
gcagactccg tgaggggccg gttcaccatc tccagagaca attccaagaa cacgctgtat     240
ttgcaaatga atagcctgag agccgaggac acggccgtat attactgtgc gaaaggacag     300
tgggaacggg gaagttacta ctttgactac tggggccggg gaaccctggt caccgtctcg     360
agtggaggcg gcggttcagg cggaggtggc tctggcggtg cggaagtgc acagtctgtg     420 ctgacgcagc cgccctcagt gtctggggcc ccagggcaga gggtcaccat ctcctgcact     480
gggagcagct ccaacatcgg gacggttat gatgtacact ggtatcagca gcttccagga     540
acagccccca aactcctcat ctatggtaac agtcatcggc cctcaggggt ccctgaccga     600
ttctctggct ccaagtctgg tacctctgcc tcctggccca tcactgggct ccaggctgag     660
gatgaggctg attattactg ccactcctat gacggcagtg tgagtggctg attttcggc      720 ggagggacca agctgaccgt cctaggtgcg gccgcacatc atcatcacca tcac          774

<210> SEQ ID NO 20
<211> LENGTH: 258
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Ile Asn Trp Val Arg Gln Ala Pro Gly Lys Gly Leu Glu Trp Val
        35                  40                  45

Ser Ala Ile Ser Val Thr Gly Gly Ser Thr Ala Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                      90                      95
Ala Lys Gly Gln Trp Glu Arg Gly Ser Tyr Tyr Phe Asp Tyr Trp Gly
            100                     105                     110

Arg Gly Thr Leu Val Thr Val Ser Gly Gly Gly Ser Gly Gly
            115                     120                     125

Gly Gly Ser Gly Gly Gly Ser Ala Gln Ser Val Leu Thr Gln Pro
            130                     135                     140

Pro Ser Val Ser Gly Ala Pro Gly Gln Arg Val Thr Ile Ser Cys Thr
145                     150                     155                     160

Gly Ser Ser Ser Asn Ile Gly Asp Gly Tyr Asp Val His Trp Tyr Gln
                        165                     170                     175

Gln Leu Pro Gly Thr Ala Pro Lys Leu Leu Ile Tyr Gly Asn Ser His
            180                     185                     190

Arg Pro Ser Gly Val Pro Asp Arg Phe Ser Gly Ser Lys Ser Gly Thr
            195                     200                     205

Ser Ala Ser Leu Ala Ile Thr Gly Leu Gln Ala Glu Asp Glu Ala Asp
            210                     215                     220

Tyr Tyr Cys His Ser Tyr Asp Gly Ser Val Ser Gly Trp Ile Phe Gly
225                     230                     235                     240

Gly Gly Thr Lys Leu Thr Val Leu Gly Ala Ala His His His His
                        245                     250                     255

His His
```

<210> SEQ ID NO 21
<211> LENGTH: 363
<212> TYPE: DNA
<213> ORGANISM: Homo sapiens

<400> SEQUENCE: 21

```
gaggtccagt tgttggagtc tgggggaggc ttggtacagc ctggggggtc cctgagactc    60
tcctgtgcag cctctggatt cacctttagt agatatgtca tcaactgggt ccgccaggct   120
ccagggaagg ggctggaatg ggtctcagct attagtgtta ctggtggtag cacggcctac   180
gcagactccg tgaggggccg gttcaccatc tccagagaca attccaagaa cacgctgtat   240
ttgcaaatga atagcctgag agccgaggac acggccgtat attactgtgc gaaggacag   300
tgggaacggg gaagttacta ctttgactac tggggccggg aaccctggt caccgtctcg   360
agt                                                                 363
```

<210> SEQ ID NO 22
<211> LENGTH: 121
<212> TYPE: PRT
<213> ORGANISM: Homo sapiens

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Ile Asn Trp Val Arg Gln Ala Pro Gly Lys Gly Leu Glu Trp Val
            35                  40                  45

Ser Ala Ile Ser Val Thr Gly Gly Ser Thr Ala Tyr Ala Asp Ser Val
            50                  55                  60

Arg Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
             85                  90                  95

Ala Lys Gly Gln Trp Glu Arg Gly Ser Tyr Tyr Phe Asp Tyr Trp Gly
        100                 105                 110

Arg Gly Thr Leu Val Thr Val Ser Ser
        115                 120

<210> SEQ ID NO 23
<211> LENGTH: 333
<212> TYPE: DNA
<213> ORGANISM: Homo sapiens

<400> SEQUENCE: 23
cagtctgtgc tgacgcagcc gccctcagtg tctggggccc cagggcagag ggtcaccatc    60
tcctgcactg ggagcagctc aacatcggg acggttatg atgtacactg gtatcagcag    120
cttccaggaa cagcccccaa actcctcatc tatggtaaca gtcatcggcc ctcaggggtc    180
cctgaccgat tctctggctc caagtctggt acctctgcct ccctggccat cactgggctc    240
caggctgagg atgaggctga ttattactgc cactcctatg acggcagtgt gagtggctgg    300
attttcggcg agggaccaa gctgaccgtc cta                                  333

<210> SEQ ID NO 24
<211> LENGTH: 111
<212> TYPE: PRT
<213> ORGANISM: Homo sapiens

<400> SEQUENCE: 24

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Asp Gly
            20                  25                  30

Tyr Asp Val His Trp Tyr Gln Gln Leu Pro Gly Thr Ala Pro Lys Leu
        35                  40                  45

Leu Ile Tyr Gly Asn Ser His Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys His Ser Tyr Asp Gly Ser
                85                  90                  95

Val Ser Gly Trp Ile Phe Gly Gly Gly Thr Lys Leu Thr Val Leu
            100                 105                 110

<210> SEQ ID NO 25
<211> LENGTH: 747
<212> TYPE: DNA
<213> ORGANISM: Homo sapiens

<400> SEQUENCE: 25
caggtgcagc tggtgcaatc tggggctgag gtgaagaagc ctggggcctc agtgaaggtt    60
tcctgcaagg catctggata caccttcacc agctactata tgcactgggt gcgacaggcc    120
cctggacaag gcttgagtg gatgggaata atcaaccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagagacgag    300
aactgggggt cgaccccctg ggccagggga acctggtca ccgtctcgag tggaggcggc    360
ggttcaggcg gaggtggctc tggcggtggc ggaagtgcac tttcctatga gctgactcag    420

| | | | |
|---|---|---|---|
| ccaccctcag tgtccgtgtc tccaggacag acagccagca ttacctgctc tggacatgca | | | 480 |
| ctgggggaca aatttgtttc ctggtatcag cagaagccag gccagtcccc tgtattggtc | | | 540 |
| atctatgacg atacccagcg gccctcaggg atccctgagc gattctctgg ctccaactct | | | 600 |
| gggaacacag ccactctgac catcagcggg acccaggcta tggatgaggc tgactattac | | | 660 |
| tgtcaggcgt gggacagcag cttcgtattc ggcggaggga ccaaggtcac cgtcctaggt | | | 720 |
| gcggccgcac atcaccatca ccatcac | | | 747 |

<210> SEQ ID NO 26
<211> LENGTH: 249
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Glu Asn Trp Gly Phe Asp Pro Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ala Leu Ser Tyr Glu Leu Thr Gln Pro Pro Ser Val
    130                 135                 140

Ser Val Ser Pro Gly Gln Thr Ala Ser Ile Thr Cys Ser Gly His Ala
145                 150                 155                 160

Leu Gly Asp Lys Phe Val Ser Trp Tyr Gln Gln Lys Pro Gly Gln Ser
                165                 170                 175

Pro Val Leu Val Ile Tyr Asp Asp Thr Gln Arg Pro Ser Gly Ile Pro
            180                 185                 190

Glu Arg Phe Ser Gly Ser Asn Ser Gly Asn Thr Ala Thr Leu Thr Ile
        195                 200                 205

Ser Gly Thr Gln Ala Met Asp Glu Ala Asp Tyr Tyr Cys Gln Ala Trp
    210                 215                 220

Asp Ser Ser Phe Val Phe Gly Gly Gly Thr Lys Val Thr Val Leu Gly
225                 230                 235                 240

Ala Ala Ala His His His His His His
                245

<210> SEQ ID NO 27
<211> LENGTH: 351
<212> TYPE: DNA
<213> ORGANISM: Homo sapiens

<400> SEQUENCE: 27

| | |
|---|---|
| caggtgcagc tggtgcaatc tggggctgag gtgaagaagc ctggggcctc agtgaaggtt | 60 |

```
tcctgcaagg catctggata caccttcacc agctactata tgcactgggt gcgacaggcc    120
cctggacaag gccttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagagacgag    300
aactgggggt cgacccctg gggccaggga accctggtca ccgtctcgag t              351
```

<210> SEQ ID NO 28
<211> LENGTH: 117
<212> TYPE: PRT
<213> ORGANISM: Homo sapiens

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Glu Asn Trp Gly Ser Thr Pro Trp Gly Gln Gly Thr Leu
            100                 105                 110

Val Thr Val Ser Ser
        115
```

<210> SEQ ID NO 29
<211> LENGTH: 315
<212> TYPE: DNA
<213> ORGANISM: Homo sapiens

<400> SEQUENCE: 29

```
tcctatgagc tgactcagcc accctcagtg tccgtgtctc caggacagac agccagcatt    60
acctgctctg gacatgcact gggggacaaa tttgtttcct ggtatcagca gaagccaggc    120
cagtcccctg tattggtcat ctatgacgat acccagcggc cctcagggat ccctgagcga    180
ttctctggct ccaactctgg gaacacagcc actctgacca tcagcgggac ccaggctatg    240
gatgaggctg actattactg tcaggcgtgg gacagcagct cgtattcgg cggagggacc    300 aaggtcaccg tccta                                                      315
```

<210> SEQ ID NO 30
<211> LENGTH: 105
<212> TYPE: PRT
<213> ORGANISM: Homo sapiens

<400> SEQUENCE: 30

```
Ser Tyr Glu Leu Thr Gln Pro Pro Ser Val Ser Val Ser Pro Gly Gln
1               5                   10                  15

Thr Ala Ser Ile Thr Cys Ser Gly His Ala Leu Gly Asp Lys Phe Val
            20                  25                  30

Ser Trp Tyr Gln Gln Lys Pro Gly Gln Ser Pro Val Leu Val Ile Tyr
        35                  40                  45
```

```
Asp Asp Thr Gln Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Phe Val Phe
                 85                  90                  95

Gly Gly Gly Thr Lys Val Thr Val Leu
            100                 105

<210> SEQ ID NO 31
<211> LENGTH: 5
<212> TYPE: PRT
<213> ORGANISM: Homo sapiens

<400> SEQUENCE: 31

Ser Tyr Tyr Met His
1               5

<210> SEQ ID NO 32
<211> LENGTH: 17
<212> TYPE: PRT
<213> ORGANISM: Homo sapiens

<400> SEQUENCE: 32

Ile Ile Asn Pro Ser Gly Gly Ser Thr Ser Tyr Ala Gln Lys Phe Gln
1               5                   10                  15

Gly

<210> SEQ ID NO 33
<211> LENGTH: 8
<212> TYPE: PRT
<213> ORGANISM: Homo sapiens

<400> SEQUENCE: 33

Asp Glu Asn Trp Gly Phe Asp Pro
1               5

<210> SEQ ID NO 34
<211> LENGTH: 11
<212> TYPE: PRT
<213> ORGANISM: Homo sapiens

<400> SEQUENCE: 34

Ser Gly His Ala Leu Gly Asp Lys Phe Val Ser
1               5                   10

<210> SEQ ID NO 35
<211> LENGTH: 7
<212> TYPE: PRT
<213> ORGANISM: Homo sapiens

<400> SEQUENCE: 35

Asp Asp Thr Gln Arg Pro Ser
1               5

<210> SEQ ID NO 36
<211> LENGTH: 7
<212> TYPE: PRT
<213> ORGANISM: Homo sapiens

<400> SEQUENCE: 36

Gln Ala Trp Asp Ser Ser Phe
1               5
```

<210> SEQ ID NO 37
<211> LENGTH: 5
<212> TYPE: PRT
<213> ORGANISM: Homo sapiens

<400> SEQUENCE: 37

Arg Tyr Val Ile Asn
1               5

<210> SEQ ID NO 38
<211> LENGTH: 17
<212> TYPE: PRT
<213> ORGANISM: Homo sapiens

<400> SEQUENCE: 38

Ala Ile Ser Val Thr Gly Gly Ser Thr Ala Tyr Ala Asp Ser Val Arg
1               5                   10                  15

Gly

<210> SEQ ID NO 39
<211> LENGTH: 12
<212> TYPE: PRT
<213> ORGANISM: Homo sapiens

<400> SEQUENCE: 39

Gly Gln Trp Glu Arg Gly Ser Tyr Tyr Phe Asp Tyr
1               5                   10

<210> SEQ ID NO 40
<211> LENGTH: 14
<212> TYPE: PRT
<213> ORGANISM: Homo sapiens

<400> SEQUENCE: 40

Thr Gly Ser Ser Ser Asn Ile Gly Asp Gly Tyr Asp Val His
1               5                   10

<210> SEQ ID NO 41
<211> LENGTH: 7
<212> TYPE: PRT
<213> ORGANISM: Homo sapiens

<400> SEQUENCE: 41

Gly Asn Ser His Arg Pro Ser
1               5

<210> SEQ ID NO 42
<211> LENGTH: 6
<212> TYPE: PRT
<213> ORGANISM: Homo sapiens

<400> SEQUENCE: 42

His Ser Tyr Asp Gly Ser
1               5

<210> SEQ ID NO 43
<211> LENGTH: 5
<212> TYPE: PRT
<213> ORGANISM: Homo sapiens

<400> SEQUENCE: 43

Ser Tyr Ala Met Ser
1               5

```
<210> SEQ ID NO 44
<211> LENGTH: 17
<212> TYPE: PRT
<213> ORGANISM: Homo sapiens

<400> SEQUENCE: 44

Ala Ile Ser Gly Ser Gly Gly Ser Thr Tyr Tyr Ala Asp Ser Val Lys
1               5                   10                  15
Gly

<210> SEQ ID NO 45
<211> LENGTH: 15
<212> TYPE: PRT
<213> ORGANISM: Homo sapiens

<400> SEQUENCE: 45

Met Gly Pro Cys Thr Gly Gly Ser Cys Tyr Asp Thr Leu Gly Asn
1               5                   10                  15

<210> SEQ ID NO 46
<211> LENGTH: 14
<212> TYPE: PRT
<213> ORGANISM: Homo sapiens

<400> SEQUENCE: 46

Thr Gly Ser Ser Ser Asn Ile Gly Ala Gly Tyr Asp Val His
1               5                   10

<210> SEQ ID NO 47
<211> LENGTH: 7
<212> TYPE: PRT
<213> ORGANISM: Homo sapiens

<400> SEQUENCE: 47

Gly Asn Gly Asn Arg Pro Ser
1               5

<210> SEQ ID NO 48
<211> LENGTH: 12
<212> TYPE: PRT
<213> ORGANISM: Homo sapiens

<400> SEQUENCE: 48

Gln Ser Tyr Asp Ser Ser Leu Ser Gly Ser Lys Val
1               5                   10

<210> SEQ ID NO 49
<211> LENGTH: 109
<212> TYPE: PRT
<213> ORGANISM: Homo sapiens

<400> SEQUENCE: 49

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Lys Met Ser
```

```
                65                  70                  75                  80
Pro Ile Asn Met Leu Tyr Phe Asn Gly Lys Glu Gln Ile Ile Tyr Gly
                    85                  90                  95

Lys Ile Pro Ala Met Val Val Asp Arg Cys Gly Cys Ser
                100                 105
```

<210> SEQ ID NO 50
<211> LENGTH: 320
<212> TYPE: DNA
<213> ORGANISM: Homo sapiens

<400> SEQUENCE: 50

```
gtcagcccaa ggctgccccc tcggtcactc tgttcccgcc ctcctctgag gagcttcaag        60
ccaacaaggc cacactggtg tgtctcataa gtgacttcta cccgggagcc gtgacagtgg       120
cctggaaggc agatagcagc cccgtcaagg cgggagtgga gaccaccaca ccctccaaac       180
aaagcaacaa caagtacgcg gccagcagct atctgagcct gacgcctgag cagtggaagt       240
cccacagaag ctacagctgc caggtcacgc atgaagggag caccgtggag aagacagtgg       300
cccctacaga atgttcatag                                                    320
```

<210> SEQ ID NO 51
<211> LENGTH: 106
<212> TYPE: PRT
<213> ORGANISM: Homo sapiens

<400> SEQUENCE: 51

```
Gly Gln Pro Lys Ala Ala Pro Ser Val Thr Leu Phe Pro Pro Ser Ser
  1               5                  10                  15
Glu Glu Leu Gln Ala Asn Lys Ala Thr Leu Val Cys Leu Ile Ser Asp
                 20                  25                  30
Phe Tyr Pro Gly Ala Val Thr Val Ala Trp Lys Ala Asp Ser Ser Pro
             35                  40                  45
Val Lys Ala Gly Val Glu Thr Thr Thr Pro Ser Lys Gln Ser Asn Asn
         50                  55                  60
Lys Tyr Ala Ala Ser Ser Tyr Leu Ser Leu Thr Pro Glu Gln Trp Lys
 65                  70                  75                  80
Ser His Arg Ser Tyr Ser Cys Gln Val Thr His Glu Gly Ser Thr Val
                 85                  90                  95
Glu Lys Thr Val Ala Pro Thr Glu Cys Ser
                100                 105
```

<210> SEQ ID NO 52
<211> LENGTH: 992
<212> TYPE: DNA
<213> ORGANISM: Homo sapiens

<400> SEQUENCE: 52

```
cctccaccaa gggcccatcg gtcttccccc tggcaccctc ctccaagagc acctctgggg        60
gcacagcggc cctgggctgc ctggtcaagg actacttccc cgaaccggtg acggtgtcgt       120
ggaactcagg cgccctgacc agcggcgtgc acaccttccc ggctgtccta cagtcctcag       180
gactctactc cctcagcagc gtggtgaccg tgccctccag cagcttgggc acccagacct       240
acatctgcaa cgtgaatcac aagcccagca acaccaaggt ggacaagaaa gttgagccca       300
aatcttgtga caaaactcac acatgcccac cgtgcccagc acctgaactc ctggggggac       360
cgtcagtctt cctcttcccc ccaaaaccca aggacaccct catgatctcc cggacccctg       420
```

```
aggtcacatg cgtggtggtg gacgtgagcc acgaagaccc tgaggtcaag ttcaactggt    480
acgtggacgg cgtggaggtg cataatgcca agacaaagcc gcgggaggag cagtacaaca    540
gcacgtaccg tgtggtcagc gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggaggaga    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctata gcaagctcac cgtggacaag agcaggtggc    900
agcaggggaa cgtcttctca tgctccgtga tgcatgaggc tctgcacaac cactacacgc    960
agaagagcct ctccctgtcc ccgggtaaat ga                                  992
```

<210> SEQ ID NO 53
<211> LENGTH: 330
<212> TYPE: PRT
<213> ORGANISM: Homo Sapiens

<400> SEQUENCE: 53

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 6
<212> TYPE: PRT
<213> ORGANISM: Any
<220> FEATURE:
<221> NAME/KEY: MISC_FEATURE
<222> LOCATION: (2)..(3)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid

<400> SEQUENCE: 54

Lys Xaa Xaa Pro Xaa Asn
1               5
```

NEUTRALIZING ANTIBODIES AGAINST GDF-8 AND USES THEREFOR

This application is a divisional application of U.S. patent application Ser. No. 12/632,383, now U.S. Pat. No. 8,420,082, filed on Dec. 7, 2009, which is a divisional application of U.S. patent application Ser. No. 11/777,525, now U.S. Pat. No. 7,655,763, filed Jul. 13, 2007, which is a divisional application of U.S. patent application Ser. No. 10/688,925, now U.S. Pat. No. 7,261,893, filed Oct. 21, 2003, which claims priority to U.S. provisional patent application No. 60/419,964, filed Oct. 22, 2012, all of which are incorporated herein by reference in their entireties.

TECHNICAL FIELD

The technical field relates to antibodies against growth and differentiation factor-8 (GDF-8), in particular human antibodies, and antibody fragments, especially those that inhibit GDF-8 activity in vitro and/or in vivo. The field further relates to diagnosing, preventing, or treating degenerative disorders of muscle or bone, or disorders of insulin metabolism.

BACKGROUND

Growth and differentiation factor-8 (GDF-8), also known as myostatin, is a secreted protein and is a member of the transforming growth factor-beta (TGF-β) superfamily of structurally related growth factors, all of which possess physiologically important growth-regulatory and morphogenetic properties (Kingsley et al. (1994) Genes Dev., 8: 133-146; Hoodless et al. (1998) Curr. Topics Microbiol. Immunol., 228: 235-272). Similarly to TGF-β, human GDF-8 is synthesized as a 375 amino acid long precursor protein. The precursor GDF-8 protein forms a homodimer. During processing the amino-terminal propeptide is cleaved off at Arg-266. The cleaved propeptide, known as the "latency-associated peptide" (LAP), may remain noncovalently bound to the homodimer, thereby inactivating the complex (Miyazono et al. (1988) J. Biol. Chem., 263: 6407-6415; Wakefield et al. (1988) J. Biol. Chem., 263: 7646-7654; Brown et al. (1990) Growth Factors, 3: 35-43; and Thies et al. (2001) Growth Factors, 18: 251-259). The complex of mature GDF-8 with propeptide is commonly referred to as the "small latent complex" (Gentry et al. (1990) Biochemistry, 29: 6851-6857; Derynck et al. (1995) Nature, 316: 701-705; and Massague (1990) Ann. Rev. Cell Biol., 12: 597-641). Other proteins are also known to bind to mature GDF-8 and inhibit its biological activity. Such inhibitory proteins include follistatin and follistatin-related proteins (Gamer et al. (1999) Dev. Biol., 208: 222-232).

An alignment of deduced amino acid sequences from various species demonstrates that GDF-8 is highly conserved throughout evolution (McPherron et al. (1997) Proc. Nat. Acad. Sci. U.S.A., 94: 12457-12461). In fact, the sequences of human, mouse, rat, porcine, and chicken GDF-8 are 100% identical in the C-terminal region, while in baboon, bovine, and ovine they differ only by 3 amino acids. The zebrafish GDF-8 is the most diverged; however, it is still 88% identical to human.

The high degree of conservation suggests that GDF-8 has an essential function. GDF-8 is highly expressed in the developing and adult skeletal muscle and was found to be involved in the regulation of critical biological processes in the muscle and in osteogenesis. For example, GDF-8 knockout transgenic mice are characterized by a marked hypertrophy and hyperplasia of the skeletal muscle (McPherron et al. (1997) Nature, 387: 83-90) and altered cortical bone structure (Hamrick et al. (2000) Bone, 27 (3): 343-349). Similar increases in skeletal muscle mass are evident in naturally occurring mutations of GDF-8 in cattle (Ashmore et al. (1974) Growth, 38: 501-507; Swatland et al. (1994) J. Anim. Sci., 38: 752-757; McPherron et al. (1997) Proc. Nat. Acad. Sci. U.S.A., 94: 12457-12461; and Kambadur et al. (1997) Genome Res., 7: 910-915). Studies have indicated that muscle wasting associated with HIV-infection is accompanied by an increase in GDF-8 expression (Gonzalez-Cadavid et al. (1998) Proc. Nat. Acad. Sci. U.S.A., 95: 14938-14943). GDF-8 has also been implicated in the production of muscle-specific enzymes (e.g., creatine kinase) and proliferation of myoblast cells (WO 00/43781). In addition to its growth-regulatory and morphogenetic properties, GDF-8 is thought to be also involved in a number of other physiological processes, including glucose homeostasis in the development of type 2 diabetes, impaired glucose tolerance, metabolic syndromes (e.g., syndrome X), insulin resistance induced by trauma, such as burns or nitrogen imbalance, and adipose tissue disorders (e.g., obesity) (Kim et al. (2001) BBRC, 281: 902-906).

A number of human and animal disorders are associated with functionally impaired muscle tissue, e.g., muscular dystrophy (including Duchenne's muscular dystrophy), amyotrophic lateral sclerosis (ALS), muscle atrophy, organ atrophy, frailty, congestive obstructive pulmonary disease, sarcopenia, cachexia, and muscle wasting syndromes caused by other diseases and conditions. To date, very few reliable or effective therapies have been developed to treat these disorders.

There are also a number of conditions associated with a loss of bone, which include osteoporosis and osteoarthritis, especially in the elderly and/or postmenopausal women. In addition, metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. Currently available therapies for these conditions work by inhibiting bone resorption. A therapy that promotes new bone formation would be a desirable alternative to these therapies.

Thus, a need exists to develop new therapies that contribute to an overall increase of muscle mass and/or strength and/or bone density, especially, in humans.

SUMMARY

It is one of the objects of the present invention to provide safe and effective therapeutic methods for muscle and/or bone-associated disorders.

It is another object of the invention to provide methods of increasing muscle mass and/or bone strength and/or density in vertebrates.

It is yet another object of the invention to provide inhibitors of GDF-8 that are safe and effective in vivo.

Still another object of the invention is to provide human antibodies and fragments thereof that bind GDF-8 with high specificity and affinity.

Thus, methods for treating muscle and bone degenerative disorders are provided. The methods are also useful for increasing muscle mass and bone density in normal animals. Also provided are novel human anti-GDF-8 antibodies, termed Myo29, Myo28, and Myo22, and antibodies and antigen-binding fragments derived therefrom. The antibodies of the invention possess a number of useful properties. First, the antibodies are capable of binding mature GDF-8 with high affinity. Second, the disclosed antibodies inhibit GDF-8 activity in vitro and in vivo as demonstrated, for example, by inhibition of ActRIIB binding and reporter gene assays. Third, the disclosed antibodies may inhibit GDF-8 activity associated with negative regulation of skeletal muscle mass and bone density.

Certain embodiments of the invention comprise the $V_H$ and/or $V_L$ domain of the Fv fragment of Myo29, Myo28, or Myo22. Further embodiments comprise one or more complementarity determining regions (CDRs) of any of these $V_H$ and $V_L$ domains. Other embodiments comprise an H3 fragment of the $V_H$ domain of Myo29, Myo28, or Myo22.

Other aspects provide compositions containing antibodies of the invention or their antigen-binding fragments, and their use in methods of inhibiting or neutralizing GDF-8, including methods of treatment of the human or animals. The antibodies of the invention may be used to treat or prevent conditions in which an increase in muscle tissue or bone density is desirable. For example, the presently disclosed antibodies may be used in therapies to repair damaged muscle, e.g., myocardium, diaphragm, etc. Exemplary disease and disorders include muscle and neuromuscular disorders such as muscular dystrophy (including Duchenne's muscular dystrophy); amyotrophic lateral sclerosis; muscle atrophy; organ atrophy; frailty; tunnel syndrome; congestive obstructive pulmonary disease; sarcopenia, cachexia, and other muscle wasting syndromes; adipose tissue disorders (e.g., obesity); type 2 diabetes; impaired glucose tolerance; metabolic syndromes (e.g., syndrome X); insulin resistance induced by trauma such as burns or nitrogen imbalance; and bone degenerative diseases (e.g., osteoarthritis and osteoporosis).

In addition, the presently disclosed antibodies may be used as a diagnostic tool to quantitatively or qualitatively detect GDF-8 or its fragments in a biological sample. The presence or amount of GDF-8 detected can be correlated with one or more of the medical conditions listed above.

Another aspect provides an isolated nucleic acid, which comprises a sequence encoding a $V_H$ or $V_L$ domain from an Fv fragment of Myo29, Myo28, or Myo22. An isolated nucleic acid, which comprises a sequence encoding at least one CDR from any of the presently disclosed $V_H$ and $V_L$ domains, is also disclosed. Another aspect provides host cells comprising such nucleic acid.

Yet another aspect provides a method of producing new $V_H$ and $V_L$ domains and/or functional antibodies comprising all or a portion of such domains derived from the $V_H$ or $V_L$ domains of Myo29, Myo28, or Myo22.

Additional objects of the invention will be set forth in part in the description which follows, and in part will be obvious from the description, or may be learned by practice of the invention. Various objects, aspects, and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

FIGS. 4B and 4C show that Myo29 reduces the GDF-8 activity in a dose-responsive manner, with an $IC_{50}$ of 15-30 ng/ml, and inhibits the biological activity of BMP-11 to the same extent. FIG. 4D illustrates that Myo29 does not affect the activity of activin in this assay.

DETAILED DESCRIPTION

I. Definitions

Figure 1:
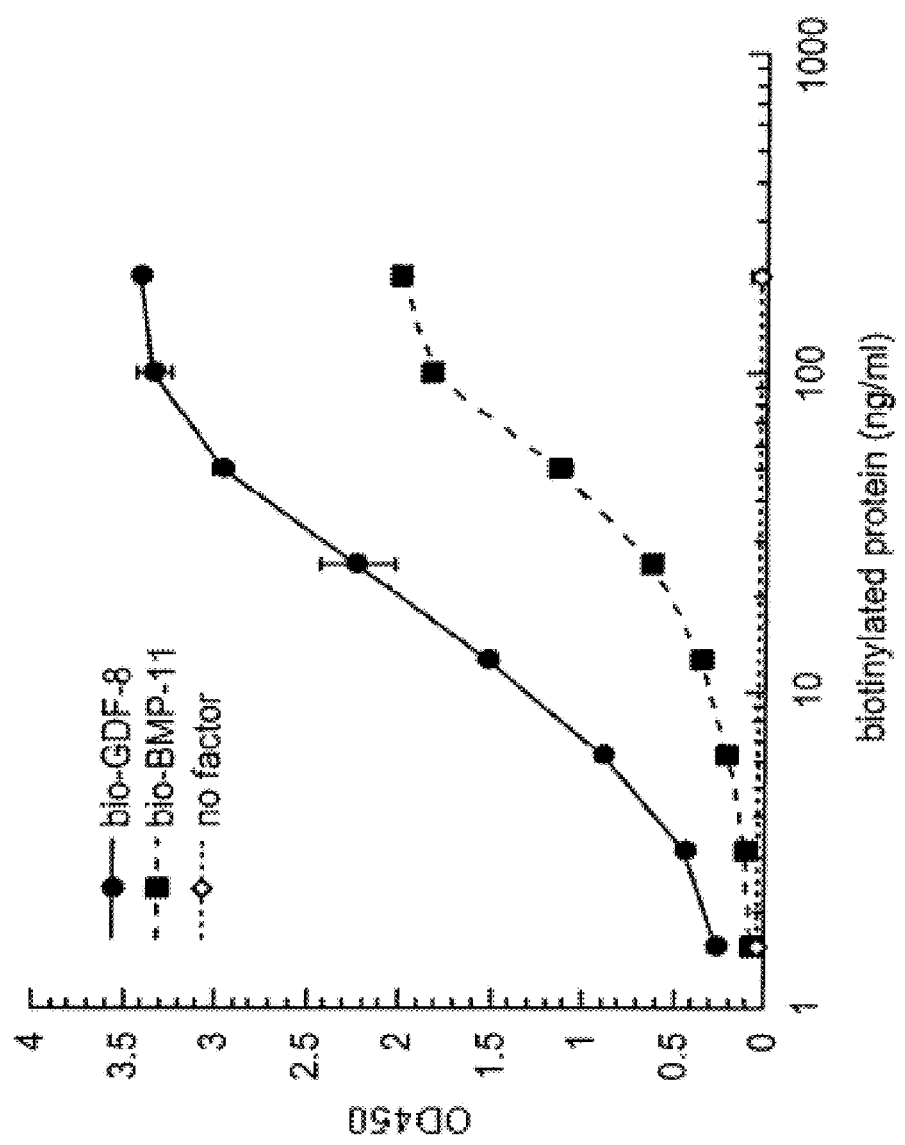
FIG. 1 shows that biotinylated GDF-8 and BMP-11 bind the ActRIIB receptor with an $ED_{50}$ of 15 ng/ml and 40 ng/ml, respectively.

The term "antibody," as used herein, refers to an immunoglobulin or a part thereof, and encompasses any polypeptide comprising an antigen-binding site regardless of the source, species of origin, method of production, and characteristics. As a non-limiting example, the term "antibody" includes human, orangutan, mouse, rat, goat, sheep, and chicken antibodies. The term includes but is not limited to polyclonal, monoclonal, monospecific, polyspecific, non-specific, humanized, single-chain, chimeric, synthetic, recombinant, hybrid, mutated, and CDR-grafted antibodies. For the purposes of the present invention, it also includes, unless otherwise stated, antibody fragments such as Fab, F(ab)$_2$, Fv, scFv, Fd, dAb, and other antibody fragments that retain the antigen-binding function.

Antibodies can be made, for example, via traditional hybridoma techniques (Kohler and Milstein (1975) Nature, 256: 495-499), recombinant DNA methods (U.S. Pat. No. 4,816, 567), or phage display techniques using antibody libraries (Clackson et al. (1991) Nature, 352: 624-628; Marks et al. (1991) J. Mol. Biol., 222: 581-597). For various other antibody production techniques, see Antibodies: A Laboratory Manual, eds. Harlow et al., Cold Spring Harbor Laboratory, 1988.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a $V_H$ domain). An antigen-binding domain comprises an antibody light chain variable region ($V_L$) and an antibody heavy chain variable region ($V_H$).

The term "repertoire" refers to a genetically diverse collection of nucleotides, e.g., DNA, sequences derived wholly or partially from sequences which encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation and in response to which rearrangement occurs. Alternatively, part or all of the sequences may be obtained by combining, e.g., unrearranged V segments with D and J segments, by nucleotide synthesis, randomised mutagenesis, and other methods as disclosed in U.S. Pat. No. 5,565,332.

The term "specific interaction," or "specifically binds," or the like, means that two molecules form a complex that is relatively stable under physiologic conditions. The term is also applicable where, e.g., an antigen-binding domain is specific for a particular epitope, which is carried by a number of antigens, in which case the antibody carrying the antigen-binding domain will be able to bind to the various antigens carrying the epitope. Thus, an antibody may specifically bind, for example, BMP-11 and GDF-8 as long as it binds to the epitope, which is carried by both.

Specific binding is characterized by a high affinity and a low to moderate capacity. Nonspecific binding usually has a low affinity with a moderate to high capacity. Typically, the binding is considered specific when the affinity constant $K_a$ is higher than $10^6$ M$^{-1}$, or preferably higher than $10^8$ M$^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc. Exemplary conditions are set forth in Examples 4, 7, and 10.

The phrase "substantially as set out" means that the relevant CDR, $V_H$, or $V_L$ domain will be either identical or highly similar to the specified regions of which the sequence is set out herein. For example, such substitutions include 1 or 2 out of any 5 amino acids in the sequence of a CDR (H1, H2, H3, L1, L2, or L3).

The term "TGF-β superfamily" refers to a family of structurally-related growth factors. This family of related growth factors is well known in the art (Kingsley et al. (1994) Genes Dev., 8: 133-146; Hoodless et al. (1998) Curr. Topics Microbiol. Immunol., 228: 235-72). The TGF-β superfamily includes bone morphogenetic proteins (BMP), activin, inhibin, mullerian inhibiting substance, glial-derived neurotrophic factor, and a still growing number of growth and differentiation factors (GDF), such as GDF-8 (myostatin). Many of such proteins are structurally and/or functionally related to GDF-8. For example, human BMP-11, also known as GDF-11, is 90% identical to GDF-8 at the amino-acid level (Gamer et al. (1999) Dev. Biol. 208, 222-232; Nakshima et al. (1999) Mech. Dev., 80: 185-189).

The term "GDF-8" refers to a specific growth and differentiation factor-8 and, where appropriate, factors that are structurally or functionally related to GDF-8, for example, BMP-11 and other factors belonging to the TGF-β superfamily. The term refers to the full-length unprocessed precursor form of GDF-8 as well as the mature and propeptide forms resulting from post-translational cleavage. The term also refers to any fragments and variants of GDF-8 that maintain at least some biological activities associated with mature GDF-8, as discussed herein, including sequences that have been modified. The amino acid sequence of mature human GDF-8 is provided in SEQ ID NO:49. The present invention relates to GDF-8 from all vertebrate species, including, but not limited to, human, bovine, chicken, mouse, rat, porcine, ovine, turkey, baboon, and fish (for sequence information, see, e.g., McPherron et al. (1997) Proc. Nat. Acad. Sci. U.S.A., 94: 12457-12461).

The term "mature GDF-8" refers to the protein that is cleaved from the carboxy-terminal domain of the GDF-8 precursor protein. The mature GDF-8 may be present as a monomer, homodimer, or in a GDF-8 latent complex. Depending on conditions, mature GDF-8 may establish equilibrium between any or all of these different forms. In its biologically active form, the mature GDF-8 is also referred to as "active GDF-8."

The term "GDF-8 propeptide" refers to the polypeptide that is cleaved from the amino-terminal domain of the GDF-8 precursor protein. The GDF-8 propeptide is capable of binding to the propeptide binding domain on the mature GDF-8.

The term "GDF-8 latent complex" refers to the complex of proteins formed between the mature GDF-8 homodimer and the GDF-8 propeptide. It is believed that two GDF-8 propeptides associate with two molecules of mature GDF-8 in the homodimer to form an inactive tetrameric complex. The latent complex may include other GDF inhibitors in place of or in addition to one or more of the GDF-8 propeptides.

The term "GDF-8 activity" refers to one or more of physiologically growth-regulatory or morphogenetic activities associated with active GDF-8 protein. For example, active GDF-8 is a negative regulator of skeletal muscle mass. Active GDF-8 can also modulate the production of muscle-specific enzymes (e.g., creatine kinase), stimulate myoblast proliferation, and modulate preadipocyte differentiation to adipocytes. Exemplary procedures for measuring GDF-8 activity in vivo and in vitro are set forth in Examples 2, 3, 6, and 13.

The term "GDF-8 inhibitor" includes any agent capable of inhibiting activity, expression, processing, or secretion of GDF-8. Such inhibitors include proteins, antibodies, peptides, peptidomimetics, ribozymes, anti-sense oligonucleotides, double-stranded RNA, and other small molecules, which specifically inhibit GDF-8. Such inhibitors are said to "inhibit," "neutralize," or "reduce" the biological activity of GDF-8.

The terms "neutralize," "neutralizing," "inhibitory," and their cognates refer to a reduction in the activity of GDF-8 by a GDF-8 inhibitor, relative to the activity of GDF-8 in the absence of the same inhibitor. The reduction in activity is preferably at least about 10%, 20%, 30%, 40%, 50%, 60%, 70%, 80%, 90%, or higher.

The term "treatment" is used interchangeably herein with the term "therapeutic method" and refers to both therapeutic treatment and prophylactic/preventative measures. Those in need of treatment may include individuals already having a particular medical disorder as well as those who may ultimately acquire the disorder (i.e., those needing preventative measures).

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure.

The term "mammal" refers to any animal classified as such, including humans, domestic and farm animals, zoo, sports, or pet animals, such as dogs, horses, cats, sheep, pigs, cows, etc.

The term "effective dose," or "effective amount," refers to that amount of the compound that results in amelioration of symptoms in a patient or a desired biological outcome (e.g., increasing skeletal muscle mass and/or bone density). Such amount should be sufficient to reduce the activity of GDF-8 associated with negative regulation of skeletal muscle mass and bone density. The effective amount can be determined as described in the subsequent sections.

II. Antibodies Against GDF-8 and Antigen-Binding Fragments

A. Human Antibodies Myo29, Myo28, and Myo22

The present disclosure provides novel antibodies against GDF-8, and antigen-binding fragments thereof. Nonlimiting illustrative embodiments of such antibodies are termed Myo29, Myo28, and Myo22. These exemplary embodiments are provided in the form of human IgG$_1$ antibodies.

The antibodies of the invention possess unique and beneficial characteristics. First, these antibodies are capable of binding mature GDF-8 with high affinity. Second, the antibodies of the invention may inhibit GDF-8 activity in vitro and in vivo as demonstrated, for example, by inhibition of ActRIIB binding and reporter gene assays. The antibodies of the present invention are also capable of specifically binding and/or inhibiting activity of BMP-11 as demonstrated, for example, by inhibition of ActRIIB binding and reporter gene assays. Third, the disclosed antibodies may inhibit GDF-8 activity associated with negative regulation of skeletal muscle mass and bone density.

In an exemplary embodiment, the presently disclosed antibodies are capable of specifically binding to both GDF-8 and BMP-11. It is contemplated that the antibodies may also react with other proteins, for example, those belonging to the TGF-β superfamily such as mullerian inhibiting substance, glial-derived neurotrophic factor, or growth and differentiation factors other than GDF-8. In certain embodiments, Myo29 reacts with a protein comprising a sequence identical to amino acid 72 to 88 of SEQ ID NO:49. In further embodiments, Myo29 binds to a protein comprising the sequence Lys-Xaa1-Xaa2-Pro-Xaa3-Asn (SEQ ID NO:54), wherein Xaa1, Xaa2, and Xaa3 each is any amino acid. In further embodiments, at least one of the following conditions is met: (1) Xaa1=Met, (2) Xaa2=Ser, and (3) Xaa3=Ile; all independently of each other. In other embodiments, Myo22 recognizes an epitope within the first 44 N-terminal amino acids in the sequence of mature GDF-8 (amino acids 1 through 44 of SEQ ID NO:49).

One of ordinary skill in the art will recognize that antibodies of the invention may be used to detect, measure, and inhibit proteins that differ from those stated above. In general, antibodies of the invention can be used with any protein that comprises a sequence which is at least about 70%, 80%, 90%, 95%, or more identical to any sequence of at least 100, 80, 60, 40, or 20 of contiguous amino acids in the sequence of the mature form of GDF-8 set forth SEQ ID NO:49. Nonlimiting examples of such proteins include sequences of GDF-8 derived from various species, which are described in the present specification. The percent identity is determined by standard alignment algorithms such as, for example, Basic Local Alignment Tool (BLAST) described in Altschul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

B. Variable Domains

Intact antibodies, also known as immunoglobulins, are typically tetrameric glycosylated proteins composed of two light (L) chains of approximately 25 kDa each and two heavy (H) chains of approximately 50 kDa each. Two types of light chain, termed λ and κ, are found in antibodies. Depending on the amino acid sequence of the constant domain of heavy chains, immunoglobulins can be assigned to five major classes: A, D, G, and M, and several of these may be further divided into subclasses (isotypes), e.g., IgG$_1$, IgG$_2$, IgG$_3$, IgG$_4$, IgA$_1$, and IgA$_2$. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. Briefly, each light chain is composed of an N-terminal variable (V) domain ($V_L$) and a constant (C) domain ($C_L$). Each heavy chain is composed of an N-terminal V domain, three or four C domains, and a hinge region. The $C_H$ domain most proximal to $V_H$ is designated as $C_H1$. The $V_H$ and $V_L$ domain consist of four regions of relatively conserved sequence called framework regions (FR1, FR2, FR3, and FR4), which form a scaffold for three regions of hypervariable sequence (complementarity determining regions, CDRs). The CDRs contain most of the residues responsible for specific interactions with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody-binding site. H3, for example, can be as short as two amino acid residues or greater than 26. The smallest antigen-binding fragment is the Fv, which consist of the $V_H$ and $V_L$ domains. The Fab fragment (Fragment antigen binding) consists of the $V_H$-$C_H1$ and $V_L$-$C_L$ domains covalently linked by a disulfide bond between the constant regions. To overcome the tendency of non-covalently linked $V_H$ and $V_L$ domains in the Fv to dissociate when co-expressed in a host cell, a so-called single chain (sc) Fv fragment (scFv) can be constructed, in which a flexible and adequately long polypeptide links either the C-terminus of the $V_H$ to the N-terminus of the $V_L$ or the C-terminus of the $V_L$ to the N-terminus of the $V_H$. The most commonly used linker has been a 15-residue $(Gly_4Ser)_3$ peptide, but other linkers are also known in the art.

domains, and CDRs are set forth in the Sequences Listing and are enumerated as listed in Table 1. For convenience, the positions for each CDR within $V_H$ and $V_L$ domains are listed in Table 2. The sequences of heavy and light chains excluding the $V_H$ and $V_L$ domains are identical in Myo29, Myo28, and Myo22.

TABLE 1

DNA and Amino Acid Sequences of scFv, $V_H$ and $V_L$ Domains, and CDRs

|  | Myo29 | Myo28 | Myo22 |
| --- | --- | --- | --- |
| DNA sequence of scFv | SEQ ID NO: 13 | SEQ ID NO: 7 | SEQ ID NO: 1 |
| AA sequence of scFv | SEQ ID NO: 14 | SEQ ID NO: 8 | SEQ ID NO: 2 |
| DNA sequence of VH | SEQ ID NO: 15 | SEQ ID NO: 9 | SEQ ID NO: 3 |
| AA sequence of VH | SEQ ID NO: 16 | SEQ ID NO: 10 | SEQ ID NO: 4 |
| DNA sequence of VL | SEQ ID NO: 17 | SEQ ID NO: 11 | SEQ ID NO: 5 |
| AA sequence of VL | SEQ ID NO: 18 | SEQ ID NO: 12 | SEQ ID NO: 6 |
| Germlined DNA seq. of scFv | SEQ ID NO: 25 | SEQ ID NO: 19 |  |
| Germlined AA seq. of scFv | SEQ ID NO: 26 | SEQ ID NO: 20 |  |
| Germlined DNA seq. VH | SEQ ID NO: 27 | SEQ ID NO: 21 |  |
| Germlined AA seq. of VH | SEQ ID NO: 28 | SEQ ID NO: 22 |  |
| Germlined DNA seq. of VL | SEQ ID NO: 29 | SEQ ID NO: 23 |  |
| Germlined AA seq. of VL | SEQ ID NO: 30 | SEQ ID NO: 24 |  |
| AA sequence of H1 | SEQ ID NO: 31 | SEQ ID NO: 37 | SEQ ID NO: 43 |
| AA sequence of H2 | SEQ ID NO: 32 | SEQ ID NO: 38 | SEQ ID NO: 44 |
| AA sequence of H3 | SEQ ID NO: 33 | SEQ ID NO: 39 | SEQ ID NO: 45 |
| AA sequence of L1 | SEQ ID NO: 34 | SEQ ID NO: 40 | SEQ ID NO: 46 |
| AA sequence of L2 | SEQ ID NO: 35 | SEQ ID NO: 41 | SEQ ID NO: 47 |
| AA sequence of L3 | SEQ ID NO: 36 | SEQ ID NO: 42 | SEQ ID NO: 48 |

Antibody diversity is created by the use of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random $V_H$-$V_L$ pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be generated (Immunoglobulin Genes, 2nd ed., eds. Jonio et al., Academic Press, San Diego, Calif., 1995). Because of the many processes involved in generating antibody diversity, it is unlikely that independently derived monoclonal antibodies with the same antigen specificity will have identical amino acid sequences.

Thus, the present invention further provides novel CDRs derived from human immunoglobulin gene libraries. The structure for carrying a CDR of the invention will generally be an antibody heavy or light chain sequence or a substantial portion thereof, in which the CDR is located at a location corresponding to the CDR of naturally occurring $V_H$ and $V_L$. The structures and locations of immunoglobulin variable domains may be determined as described in Sequences of Proteins of Immunological Interest, US Department of Health and Human Services, eds. Kabat et al., 1991.

DNA and amino acid (AA) sequences of the presently disclosed antibodies, their scFV fragment, $V_H$ and $V_L$

TABLE 2

Positions of CDRs within scFv's

| CDR | Myo29 (SEQ ID NO: 26) | Myo28 (SEQ ID NO: 20) | Myo22 (SEQ ID NO: 2) |
| --- | --- | --- | --- |
| H1 | 31-35 | 31-35 | 31-35 |
| H2 | 50-66 | 50-66 | 50-66 |
| H3 | 99-106 | 99-110 | 99-113 |
| L1 | 157-167 | 160-173 | 163-176 |
| L2 | 183-189 | 189-195 | 192-198 |
| L3 | 222-228 | 228-233 | 231-242 |

Presently disclosed antibodies may further comprise antibody constant regions or parts thereof. For example, a $V_L$ domain may be attached at its C-terminal end to antibody light chain constant domains including human Cκ or Cλ chains, preferably Cλ chains. Similarly, a specific antigen-binding fragment based on a $V_H$ domain may be attached at its C-terminal end to all or part of an immunoglobulin heavy chain derived from any antibody isotype, e.g., IgG, IgA, IgE, and IgM, and any of the isotype subclasses, particularly $IgG_1$ and $IgG_4$. In exemplary embodiments, antibodies comprise C-terminal fragments heavy and light chains of human $IgG_{1\lambda}$. The DNA and amino acid sequences for the C-terminal fragment of the light λ chain are set forth in SEQ ID NO:50 and SEQ ID NO:51, respectively. The DNA and amino acid sequences for the C-terminal fragment of $IgG_1$ heavy chain are set forth in SEQ ID NO:52 and SEQ ID NO:53, respectively.

Certain embodiments of the invention comprise the $V_H$ and/or $V_L$ domain of the Fv fragment of Myo29, Myo28, or Myo22. Further embodiments comprise one or more complementarity determining regions (CDRs) of any of these $V_H$ and $V_L$ domains. One embodiment comprises an H3 fragment of the $V_H$ domain of Myo29, Myo28, or Myo22. The $V_H$ and $V_L$ domains of the invention, in certain embodiments, are germlined, i.e., the framework regions (FRs) of these domains are changed using conventional molecular biology techniques to match the consensus amino acid sequences of human germline gene products. In other embodiments, the framework sequences remain diverged from the germline.

C. Modified Antibodies and Their Fragments

A further aspect of the invention provides a method for obtaining an antibody antigen-binding domain specific for GDF-8. The skilled artisan will appreciate that the antibodies of the invention are not limited to the specific sequences of $V_H$ and $V_L$ as stated in Table 1 but also include variants of these sequences that retain antigen binding ability. Such variants may be derived from the provided sequences using techniques known in the art. Amino acid substitution, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR region and testing the antibody. Such alterations can be made according to the methods described in Antibody Engineering, 2nd. ed., ed. Borrebaeck, Oxford University Press, 1995.

The method for making a $V_H$ domain which is an amino acid sequence variant of the $V_H$ domain set out herein comprises a step of adding, deleting, substituting or inserting one or more amino acids in the amino acid sequence of the presently disclosed $V_H$ domain, optionally combining the $V_H$ domain thus provided with one or more $V_L$ domains, and testing the $V_H$ domain or $V_H/V_L$ combination or combinations for specific binding to GDF-8, optionally, testing the ability of such antigen-binding domain to neutralize GDF-8 activity. The $V_L$ domain may have an amino acid sequence which is substantially as set out herein.

An analogous method may be employed in which one or more sequence variants of a $V_L$ domain disclosed herein are combined with one or more $V_H$ domains.

A further aspect of the invention provides a method of preparing an antigen-binding fragment that specifically reacts with GDF-8. The method comprises:
(a) providing a starting repertoire of nucleic acids encoding a $V_H$ domain which either include a CDR3 to be replaced or lack a CDR3 encoding region;
(b) combining the repertoire with a donor nucleic acid encoding an amino acid sequence substantially as set out herein for a $V_H$ CDR3 (i.e., H3) such that the donor nucleic acid is inserted into the CDR3 region in the repertoire so as to provide a product repertoire of nucleic acids encoding a $V_H$ domain;
(c) expressing the nucleic acids of the product repertoire;
(d) selecting a specific antigen-binding fragment specific for GDF-8; and
(e) recovering the specific antigen-binding fragment or nucleic acid encoding it.

Again, an analogous method may be employed in which a $V_L$ CDR3 (i.e., L3) of the invention is combined with a repertoire of nucleic acids encoding a $V_L$ domain, which either include a CDR3 to be replaced or lack a CDR3 encoding region.

A coding sequence CDR of the invention (e.g., CDR3) may be introduced into a repertoire of variable domains lacking a CDR (e.g., CDR3), using recombinant DNA technology. For example, Marks et al. (Bio/Technology (1992) 10: 779-783) describe methods of producing repertoires of antibody variable domains in which consensus primers directed at or adjacent to the 5' end of the variable domain area are used in conjunction with consensus primers to the third framework region of human $V_H$ genes to provide a repertoire of $V_H$ variable domains lacking a CDR3. The repertoire may be combined with a CDR3 of a particular antibody. Using analogous techniques, the CDR3-derived sequences of the present invention may be shuffled with repertoires of $V_H$ or $V_L$ domains lacking a CDR3, and the shuffled complete $V_H$ or $V_L$ domains combined with a cognate $V_L$ or $V_H$ domain to provide specific antigen-binding fragments of the invention. The repertoire may then be displayed in a suitable host system such as the phage display system of WO 92/01047 so that suitable antigen-binding fragments can be selected.

Analogous shuffling or combinatorial techniques are also disclosed by Stemmer (Nature (1994) 370: 389-391), who describes the technique in relation to a β-lactamase gene but observes that the approach may be used for the generation of antibodies.

A further alternative is to generate novel $V_H$ or $V_L$ regions carrying a CDR-derived sequences of the invention using random mutagenesis of one or more selected $V_H$ and/or $V_L$ genes to generate mutations within the entire variable domain. Such a technique is described by Gram et al. (Proc. Nat. Acad. Sci. U.S.A. (1992) 89: 3576-3580), who used error-prone PCR.

Another method that may be used is to direct mutagenesis to CDR regions of $V_H$ or $V_L$ genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of $V_H$ or $V_L$ domains which are then screened for a specific binding partner or binding fragments specific for GDF-8.

A substantial portion of an immunoglobulin variable domain will comprise at least the CDR regions and, optionally, their intervening framework regions from the $scF_v$ fragments as set out herein. The portion will also include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of specific antigen-binding fragments of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example, in the production of diabodies) or protein labels as discussed in more details below.

Although the embodiments illustrated in Examples comprise a "matching" pair of $V_H$ and $V_L$ domains, the invention also encompasses binding fragments containing a single variable domain derived from either $V_H$ or $V_L$ domain sequences, especially $V_H$ domains. In the case of either of the single chain specific binding domains, these domains may be used to screen for complementary domains capable of forming a two-domain specific antigen-binding domain capable of binding GDF-8. This may be achieved by phage display screening methods using the so-called hierarchical dual combinatorial approach as disclosed in WO 92/01047 in which an individual colony containing either an H or L chain clone is used to infect a complete library of clones encoding the other chain (L or H) and the resulting two-chain specific antigen-binding domain is selected in accordance with phage display techniques such as those described in that reference. This technique is also disclosed in Marks et al., supra.

Antibodies can be conjugated by chemical methods with radionuclides, drugs, macromolecules, or other agents or can be made as fusion proteins comprising one or more CDRs of the invention.

An antibody fusion protein contains a $V_H$-$V_L$ pair where one of these chains (usually $V_H$) and another protein are synthesized as a single polypeptide chain. These types of products differ from antibodies in that they generally have an additional functional element; the active moiety of a small molecule or the principal molecular structural feature of the conjugated or fused macromolecule.

In addition to the changes to the amino acid sequence outlined above, the antibodies can be glycosylated, pegylated, or linked to albumin or a nonproteinaceous polymer. For instance, the presently disclosed antibodies may be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies are chemically modified by covalent conjugation to a polymer to increase their circulating half-life, for example. Exemplary polymers, and methods to attach them to peptides are also shown in U.S. Pat. Nos. 4,766,106; 4,179,337; 4,495,285; and 4,609,546.

In other embodiments, the antibody may be modified to have an altered glycosylation pattern (i.e., altered from the original or native glycosylation pattern). As used herein, "altered" means having one or more carbohydrate moieties deleted, and/or having one or more glycosylation sites added to the original antibody. Addition of glycosylation sites to the presently disclosed antibodies accomplished by altering the amino acid sequence to contain glycosylation site consensus sequences are well known in the art. Another means of increasing the number of carbohydrate moieties on the antibodies is by chemical or enzymatic coupling of glycosides to the amino acid residues of the antibody. These methods are described in WO 87/05330, and in Aplin and Wriston (1981) CRC Crit. Rev. Biochem., 22: 259-306. Removal of any carbohydrate moieties present on the antibodies may be accomplished chemically or enzymatically as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350.

Antibodies of the invention may also be tagged with a detectable or functional label. Detectable labels include radiolabels such as $^{131}I$ or $^{99}Tc$, which may be attached to antibodies of the invention using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

Antibodies, in which CDR sequences differ only insubstantially from those set out in SEQ ID NO: n, wherein n is 2, 4, 6, 8, 10, 12, 14, 16, 18, 20, 22, 24, 26, 28, 30, 31, 32, 33, 34, 35, 36, 37, 38, 39, 40, 41, 42, 43, 44, 45, 46, 47, or 48, are encompassed within the scope of this invention. Insubstantial differences include minor amino acid changes, such substitutions of 1 or 2 out of any 5 amino acids in the sequence of a CDR. Typically, an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a non-human derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immun. 147: 2657-2662 and Morgan et al. (1995) Immunology 86: 319-324), or changing the species from which the constant region is derived. Antibodies may have mutations in the $C_H2$ region of the heavy chain that reduce or alter effector function, e.g., Fc receptor binding and complement activation. For example, antibodies may have mutations such as those described in U.S. Pat. Nos. 5,624,821 and 5,648,260. In the $IgG_1$ or $IgG_2$ heavy chain, for example, such mutations may be made at amino acid residues 117 and 120 of SEQ ID NO:53, which represents the Fc portion of $IgG_1$ (these residues correspond to amino acids 234 and 237 in the full-length sequence of $IgG_1$ or $IgG_2$). Antibodies may also have mutations that stabilize the disulfide bond between the two heavy chains of an immunoglobulin, such as mutations in the hinge region of $IgG_4$, as disclosed in Angal et al. (1993) Mol. Immunol. 30: 105-108.

D. Nucleic Acids, Cloning and Expression Systems

The present invention further provides an isolated nucleic acid encoding antibodies or binding fragments of the present invention. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The nucleic acid of the invention comprises a coding sequence for a CDR or $V_H$ or $V_L$ domain of the invention as set forth herein.

The present invention also provides constructs in the form of plasmids, vectors, transcription or expression cassettes which comprise at least one nucleic acid of the invention as above.

The present invention also provides a host cell, which comprises one or more constructs as above. A nucleic acid encoding any CDR (H1, H2, H3, L1, L2, or L3), $V_H$ or $V_L$ domain, or specific antigen-binding fragment as provided herein forms an aspect of the present invention, as does a method of production of the encoded product. The method comprises expression from the encoding nucleic acid. Expression may be achieved by culturing under appropriate conditions recombinant host cells containing the nucleic acid. Following production by expression a $V_H$ or $V_L$ domain, or specific antigen-binding fragment may be isolated and/or purified using any suitable technique, then used as appropriate.

Specific antigen-binding fragments, $V_H$ and/or $V_L$ domains, and encoding nucleic acid molecules and vectors according to the present invention may be provided isolated and/or purified, e.g., from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known. Suitable host cells include bacteria, mammalian cells, and yeast and baculovirus systems. Mammalian cell lines available in the art for expression of a heterologous polypeptide include Chinese hamster ovary cells, HeLa cells, baby hamster kidney cells, NS0 mouse melanoma cells and many others. A common bacterial host is *E. coli*. For cells suitable for producing antibodies, see Gene Expression Systems, eds. Fernandez et al., Academic Press, 1999. Any cell compatible with the present invention may be used to produce the presently disclosed antibodies.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Molecular Cloning: a Laboratory Manual: 2nd ed., Sambrook et al., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd ed., Ausubel et al. eds., John Wiley & Sons, 1992.

Thus, a further aspect of the present invention provides a host cell comprising nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g., by culturing host cells under conditions for expression of the gene.

E. Biological Deposits

*E. coli* cultures individually transformed with the phagemid vector pCANTAB6 encoding nongermlined scFv's Myo29, Myo28, or Myo22 were deposited on Oct. 2, 2002, at American Tissue Culture Collection (ATCC) under respective Deposit Designation Numbers PTA-4741, PTA-4740, and PTA-4739. The address of the depository is 10801 University Blvd, Manassas, Va. 20110, U.S.A.

II. Methods of Treating Disease and Other Uses

The antibodies of the present invention are useful to prevent, diagnose, or treat various medical disorders in humans or animals. The antibodies can be used to inhibit or reduce one or more activities associated with GDF-8, or a related protein. Most preferably, the antibodies inhibit or reduce one or more of the activities of GDF-8 relative to the GDF-8 that is not bound by an antibody. In certain embodiments, the activity of GDF-8, when bound by one or more of the presently disclosed antibodies, is inhibited at least 50%, preferably at least 60, 62, 64, 66, 68, 70, 72, 72, 76, 78, 80, 82, 84, 86, or 88%, more preferably at least 90, 91, 92, 93, or 94%, and even more preferably at least 95% to 100% relative to a mature GDF-8 protein that is not bound by one or more of the presently disclosed antibodies. Inhibition of GDF-8 activity can be measured in pGL3(CAGA)$_{12}$ reporter gene assays (RGA) as described in Thies et al. (Growth Factors (2001) 18: 251-259) and as illustrated in Examples 2 and 9, or in ActRIIB receptor assays as illustrated in Examples 3 and 6.

The medical disorder being diagnosed, treated, or prevented by the presently disclosed antibodies is a muscle or neuromuscular disorder; an adipose tissue disorder such as obesity; type 2 diabetes; impaired glucose tolerance; metabolic syndromes (e.g., syndrome X); insulin resistance induced by trauma such as burns or nitrogen imbalance; or bone degenerative disease such as osteoporosis.

Other medical disorders being diagnosed, treated, or prevented by the presently disclosed antibodies are disorders associated with a loss of bone, which include osteoporosis, especially in the elderly and/or postmenopausal women, glucocorticoid-induced osteoporosis, osteopenia, osteoarthritis, and osteoporosis-related fractures. Other target metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. The antibodies are preferably used to prevent, diagnose, or treat such medical disorders in mammals, especially, in humans.

The antibodies or antibody compositions of the present invention are administered in therapeutically effective amounts. Generally, a therapeutically effective amount may vary with the subject's age, condition, and sex, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices are preferred.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any antibody used in the present invention, the therapeutically effective dose can be estimated initially from cell culture assays. A dose may be formulated in animal models to achieve a circulating plasma concentration range that includes the $IC_{50}$ (i.e., the concentration of the test antibody which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription-based assays, GDF-8 protein/receptor binding assays, creatine kinase assays, assays based on the differentiation of pre-adipocytes, assays based on glucose uptake in adipocytes, and immunological assays.

Generally, the compositions are administered so that antibodies or their binding fragments are given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg to 1 mg/kg, and 500 µg/kg to 1 mg/kg. Preferably, the antibodies are given as a bolus dose, to maximize the circulating levels of antibodies for the greatest length of time after the dose. Continuous infusion may also be used after the bolus dose.

The methods of treating, diagnosing, or preventing the above medical conditions with the presently disclosed antibodies can also be used on other proteins in the TGF-β superfamily. Many of these proteins are related in structure to GDF-8, such as BMP-11. Accordingly, another embodiment provides methods of treating the aforementioned disorders by administering to a subject an antibody capable of inhibiting BMP-11 or activin, either alone or in combination with other TGF-β inhibitors, such as a neutralizing antibody against GDF-8. The antibodies of the invention may also be used to treat a disease or condition associated with or mediated by BMP-11. See, e.g., U.S. Pat. Nos. 5,639,638 and 6,437,111.

The antibodies of the present invention may be used to detect the presence of proteins belonging to the TGF-β superfamily, such as BMP-11 and GDF-8, in vivo or in vitro. By correlating the presence or level of these proteins with a medical condition, one of skill in the art can diagnose the associated medical condition. The medical conditions that may be diagnosed by the presently disclosed antibodies are set forth above.

Such detection methods are well known in the art and include ELISA, radioimmunoassay, immunoblot, Western blot, immunofluorescence, immunoprecipitation, and other comparable techniques. The antibodies may further be provided in a diagnostic kit that incorporates one or more of these techniques to detect a protein (e.g., GDF-8). Such a kit may contain other components, packaging, instructions, or other material to aid the detection of the protein and use of the kit.

Where the antibodies are intended for diagnostic purposes, it may be desirable to modify them, for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable labels may include biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Yet another aspect of the invention provides a method of identifying therapeutic agents useful in treatment of muscle and bone disorders. Appropriate screening assays, e.g., ELISA-based assays, are known in the art. In such a screening assay, a first binding mixture is formed by combining an antibody of the invention and a ligand, e.g., GDF-8, BMP-11, activin; and the amount of binding between the ligand and the antibody in the first binding mixture ($M_0$) is measured. A second binding mixture is also formed by combining the antibody, the ligand, and a compound or agent to be screened, and the amount of binding between the ligand and the antibody in the second binding mixture ($M_1$) is measured. The amounts of binding in the first and second binding mixtures are then compared, for example, by calculating the $M_1/M_0$ ratio. The compound or agent is considered to be capable of inhibiting GDF-8 activity if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention.

Compounds found to reduce the antibody-ligand binding by at least about 10% (i.e., $M_1/M_0<0.9$), preferably greater than about 30%, may thus be identified and then, if desired, secondarily screened for the capacity to inhibit GDF-8 activity in other assays such as the ActRIIB binding assay (Example 2), and other cell-based and in vivo assays as described in Examples 13, 15, and 16.

III. Pharmaceutical Compositions and Methods of Administration

The present invention provides compositions comprising the presently disclosed antibodies. Such compositions may be suitable for pharmaceutical use and administration to patients. The compositions typically comprise one or more antibodies of the present invention and a pharmaceutically acceptable excipient. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. It may also be possible to obtain compositions which may be topically or orally administered, or which may be capable of transmission across mucous membranes. The administration may, for example, be intravenous, intraperitoneal, intramuscular, intracavity, subcutaneous or transdermal.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor™ EL (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the antibodies can be incorporated with excipients and used in the form of tablets, or capsules. Pharmaceutically compatible binding agents, and/or adjuvant materials can be included as part of the composition. The tablets, pills, capsules, and the like can contain any of the following ingredients, or compounds of a similar nature; a binder such as microcrystalline cellulose, gum tragacanth or gelatin; an excipient such as starch or lactose; a disintegrating agent such as alginic acid, Primogel™, or corn starch; a lubricant such as magnesium stearate or Sterotes™ a glidant such as colloidal silicon dioxide; a sweetening agent such as sucrose or saccharin; or a flavoring agent such as peppermint, methyl salicylate, or orange flavoring.

For administration by inhalation, antibodies are delivered in the form of an aerosol spray from pressured container or dispenser, which contains a suitable propellant, e.g., a gas such as carbon dioxide, or a nebulizer.

Systemic administration can also be by transmucosal or transdermal means. For example, in case of antibodies that comprise the Fc portion, compositions may be capable of transmission across mucous membranes (e.g., intestine, mouth, or lungs) via the FcRn receptor-mediated pathway (U.S. Pat. No. 6,030,613). Transmucosal administration can be accomplished, for example, through the use of lozenges, nasal sprays, inhalers, or suppositories. For transdermal administration, the active compounds are formulated into ointments, salves, gels, or creams as generally known in the art. For transmucosal or transdermal administration, penetrants appropriate to the barrier to be permeated are used in the formulation. Such penetrants are generally known in the art, and include, for example, detergents, bile salts, and fusidic acid derivatives.

The presently disclosed antibodies may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of formulating such an active compound for the treatment of individuals.

The following examples provide illustrative embodiments of the invention which do not in any way limit the invention. One of ordinary skill in the art will recognize the numerous other embodiments are encompassed within the scope of the invention.

The entire contents of all references, patents and published patent applications cited throughout this application are herein incorporated by reference.

EXAMPLES

Example 1

Purification of GDF-8

Conditioned media from a selected cell line expressing recombinant human GDF-8 protein (mature GDF-8 and GDF-8 propeptide) was acidified to pH 6.5 and applied to a 80×50 mm POROS™ HQ anion exchange column in tandem to a 80×50 mm POROS™ SP cation exchange column (PerSeptive Biosystems, Foster City, Calif.). The flow through was adjusted to pH 5.0 and applied to a 75×20 mm POROS™ SP cation exchange column (PerSeptive Biosystems) and eluted with a NaCl gradient. Fractions containing the GDF-8 latent complex, as confirmed by SDS-PAGE, were pooled, acidified with trifluoroacetic acid (TFA) to pH 2-3, then brought up to 200 ml with 0.1% TFA to lower the viscosity. The pool was then applied to a 250×21.2 mm $C_5$ column (Phenomenex, Torrance, Calif.) preceded by a 60×21.2 mm guard column (Phenomenex) and eluted with a TFA/acetonitrile gradient, to separate mature GDF-8 from GDF-8 propeptide. Pooled fractions containing mature GDF-8 were concentrated by lyophilization to remove the acetonitrile and 20 ml of 0.1% TFA was added. The sample was then applied to a 250×10 mm $C_5$ column (Phenomenex) heated to 60° C. to aid in separation. This was repeated until further separation could no longer be achieved. Fractions containing mature GDF-8 were then pooled and brought up to 40% acetonitrile and applied to a 600×21.2 BioSep™ S-3000 size exclusion column (Phenomenex) preceded by a 60×21.2 guard column. Fractions containing purified mature GDF-8 were pooled and concentrated for use in subsequent experiments.

On SDS-PAGE, purified mature GDF-8 migrated as a broad band at 25 kDa under nonreducing conditions and 13 kDa under reducing conditions. A similar SDS-PAGE profile has been reported for murine GDF-8 by McPherron et al. (Proc. Nat. Acad. Sci. U.S.A. (1997) 94: 12457-12461) and reflects the dimeric nature of the mature protein. The active mature BMP-11 dimer was purified from conditioned media from a cell line expressing recombinant human BMP-11 in a similar manner.

Active mature BMP-11 was purified from conditioned media from a cell line expressing recombinant human GDF-8 propeptide/mature BMP-11 chimeric protein. The conditioned medium was loaded onto a 10 ml TALON™ column (Clonetech, Palo Alto, Calif.) in 50 mM Tris pH 8.0, 1 M NaCl at 1 ml/min. The bound protein was eluted with a 50 mM Tris pH 8.0, 1 M NaCl, 500 mM Imidazole. Pooled fractions containing the GDF-8 propeptide/BMP-11 latent complex were acidified with 10% TFA to a pH of 3. The pool was then applied to a 250×4.6 mm Jupiter C4 column (Phenomenex, Torrance, Calif.) which was heated to 60° C. for better separation of mature BMP-11 and GDF-8 propeptide, and eluted with a TFA/acetonitrile gradient. Pooled fractions containing mature BMP-11 were concentrated by lyophilization. On SDS-PAGE, purified mature BMP-11 migrated at 25 kDa under non-reducing conditions and at 12 kDa under reducing conditions.

Example 2

Biological Activity of Purified Recombinant Human GDF-8

To demonstrate the activity of GDF-8, a reporter gene assay (RGA) was developed using a reporter vector pGL3 $(CAGA)_{12}$ expressing luciferase. The CAGA sequence was previously reported to be a TGF-β responsive sequence within the promoter of the TGF-β induced gene PAI-1 (Denner et al. (1998) EMBO J., 17: 3091-3100).

A reporter vector containing 12 CAGA boxes was made using the basic luciferase reporter plasmid pGL3 (Promega, Madison, Wis.). The TATA box and transcription initiation site from the adenovirus major later promoter (−35/+10) was inserted between the BgIII and HindIII sites. Oligonucleotides containing 12 repeats of the CAGA boxes AGCCAGACA were annealed and cloned into the XhoI site. The human rhabdomyosarcoma cell line A204 (ATCC HTB-82) was transiently transfected with $pGL3(CAGA)_{12}$ using FuGENE™ 6 transfection reagent (Boehringer Manheim, Germany). Following transfection, cells were cultured on 48 well plates in McCoy's 5A medium supplemented with 2 mM glutamine, 100 U/ml streptomycin, 100 µg/ml penicillin and 10% fetal calf serum for 16 hrs. Cells were then treated with or without 10 ng/ml GDF-8 in McCoy's 5A media with glutamine, streptomycin, penicillin, and 1 mg/ml bovine serum albumin for 6 hrs at 37° C. Luciferase was quantified in the treated cells using the Luciferase Assay System (Promega).

Figure 4A:
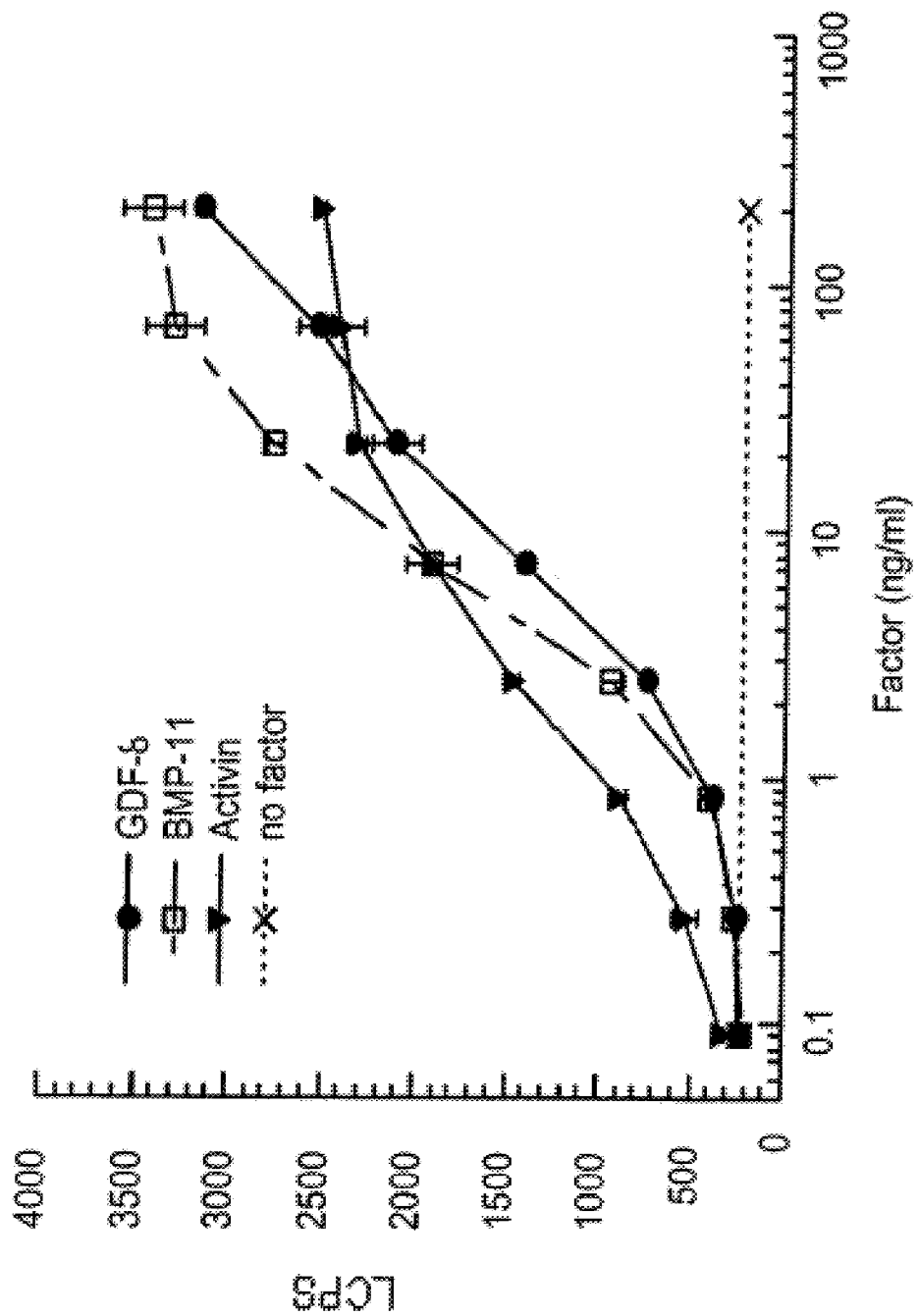
FIG. 4A demonstrates the baseline conditions, i.e., induction of the reporter gene activity by GDF-8, BMP-11, and activin.

FIG. 4A shows that GDF-8 maximally activated the reporter construct 10-fold, with an ED50 of 10 ng/ml, indicating that purified recombinant GDF-8 was biologically active. BMP-11 and activin elicited a similar biological response.

Example 3

Binding Properties of Purified GDF-8 in the ActRIIB Binding Assay

The GDF-8 latent complex was biotinylated at a ratio of 20 moles of EZ-link Sulfo-NHS-Biotin (Pierce, Rockford, Ill., Cat. No. 21217) to 1 mole of the GDF-8 complex for 2 hours on ice. The reaction was terminated by dropping the pH using 0.5% TFA and the complex was subjected to chromatography on a $C_4$ Jupiter 250×4.6 mm column (Phenomenex) to separate mature GDF-8 from GDF-8 propeptide. Biotinylated mature GDF-8 fractions eluted with a $TFA/CH_3CN$ gradient were pooled, concentrated and quantified by MicroBCA™ protein Assay Reagent Kit (Pierce, Rockford, Ill., Cat. No. 23235).

Biotinylated mature BMP-11 was prepared from BMP-11 latent complex in the same manner as described above. Recombinant ActRIIB-Fc chimera (R&D Systems, Minneapolis, Minn., Cat. No. 339-RB/CF) was coated on 96-well flat-bottom assay plates (Costar, NY, Cat. No. 3590) at 1 µg/ml in 0.2 M sodium carbonate buffer overnight at 4° C. Plates were then blocked with 1 mg/ml bovine serum albumin and washed following standard ELISA protocol. 100 µl aliquots of biotinylated GDF-8 or BMP-11 at various concentrations were added to the blocked ELISA plate, incubated for 1 hr, washed, and the amount of bound GDF-8 or BMP-11 was detected by Streptavidin-Horseradish peroxidase (SA-HRP, BD PharMingen, San Diego, Calif., Cat. No. 13047E) followed by the addition of TMB (KPL, Gaithersburg, Md., Cat. No. 50-76-04). Colorimetric measurements were done at 450 nM in a Molecular Devices microplate reader.

As shown in FIG. 1, biotinylated GDF-8 and BMP-11 bound to ActRIIB, the putative GDF-8 type II receptor with an $ED_{50}$ of 15 and 40 ng/ml, respectively, indicating that the ActRIIB binding assay is a sensitive in vitro binding assay for GDF-8 and BMP11.

Example 4

Isolation of Myo22 by Panning of scFv Libraries on GDF-8

An scFv phagemid library, which is an expanded version of the $1.38 \times 10^{10}$ library described (Vaughan et al. (1996) Nature Biotech., 14: 309-314), was used to select antibodies specific for GDF-8. Soluble GDF-8 protein (at 10 µg/ml in 50 mM sodium carbonate buffer, pH 9.6) was coated onto wells of a microtitre plate overnight at 4° C. Wells were washed in PBS and blocked for 2 hrs at 37° C. in MPBS (3% Marvel™ skimmed milk powder in PBS). Purified phage ($10^{12}$ transducing units (tu)) in 100 l of 3% MPBS were added to blocked wells and incubated at room temperature for 1 hour. Wells were washed 10 times with PBST (PBS containing 0.1% v/v Tween™ 20), then 10 times with PBS. Bound phage particles were eluted with 100 µl of 100 mM triethylamine for 10 minutes at room temperature, then immediately neutralized with 50 µl of 1 M Tris-HCl pH 7.4. The eluted phage was used to infect 10 ml exponentially growing *E. coli* TG1. Infected cells were grown in 2TY broth for 30 minutes at 37° C. stationary, followed by 30 minutes at 37° C. with aeration, then streaked onto 2TYAG plates and incubated overnight at 30° C. Colonies were scraped off the plates into 10 ml 2TY broth and 15% glycerol added for storage at −70° C.

Glycerol stock cultures from the first round panning selection were superinfected with helper phage and rescued to give scFv antibody-expressing phage particles for the second round of panning. A total of three rounds of panning were carried out in this way.

Example 5

Selection of Myo28 and Myo29 from scFv Libraries

Soluble selections were carried out using biotinylated GDF-8 protein (bioGDF-8). BioGDF-8 was used at a concentration of 1 µg/ml. An scFv library, as described in Example 4, was used. Purified scFv phage ($10^{12}$ tu) in 100 µl 3% MPBS were blocked for 30 minutes, then biotinylated antigen was added and incubated at room temperature for 1 hour. Phage/antigen was added to 50 µl of Dynal™ M280 streptavidin magnetic beads that had been blocked for 1 hour at 37° C. in 1 ml of 3% MPBS and incubated for a further 15 minutes at room temperature. Beads were captured using a magnetic rack and washed four times in 1 ml of 3% MPBS with 0.1% (v/v) Tween™ 20 followed by three washes in PBS. After the last PBS wash, beads were resuspended in 100 µl PBS and used to infect 5 ml exponentially growing *E. coli* TG-1 cells. Cells and phage were incubated for 1 hour at 37° C. (30 minutes stationary, 30 minutes shaking at 250 rpm), and then spread on 2TYAG plates. Plates were incubated at 30° C. overnight and colonies visualized the next day. Output colonies were scraped off the plates and phage rescued as

Example 6

ActRIIB Receptor Inhibition Assay and Screen

Output colonies, obtained as described in Examples 4 and 5, were picked into 96 well plates containing 100 µl of 2TYAG. ScFv production was induced by addition of 1 mM IPTG to exponentially growing cultures and incubation overnight at 30° C. Crude scFv-containing culture supernatants were screened for the ability to inhibit the binding of bioGDF-8 to ActRIIB essentially as described in Example 3. The assay was modified slightly in that binding of bioGDF-8 was detected with Europium-labeled streptavidin and using the DELFIA™ reagent kit (PerkinElmer Life Sciences, Boston, Mass.) in time-resolved fluorometric assays (TRF). Positive clones, showing inhibition of binding signal greater than irrelevant clones, were picked and assayed to confirm activity.

Figure 2:
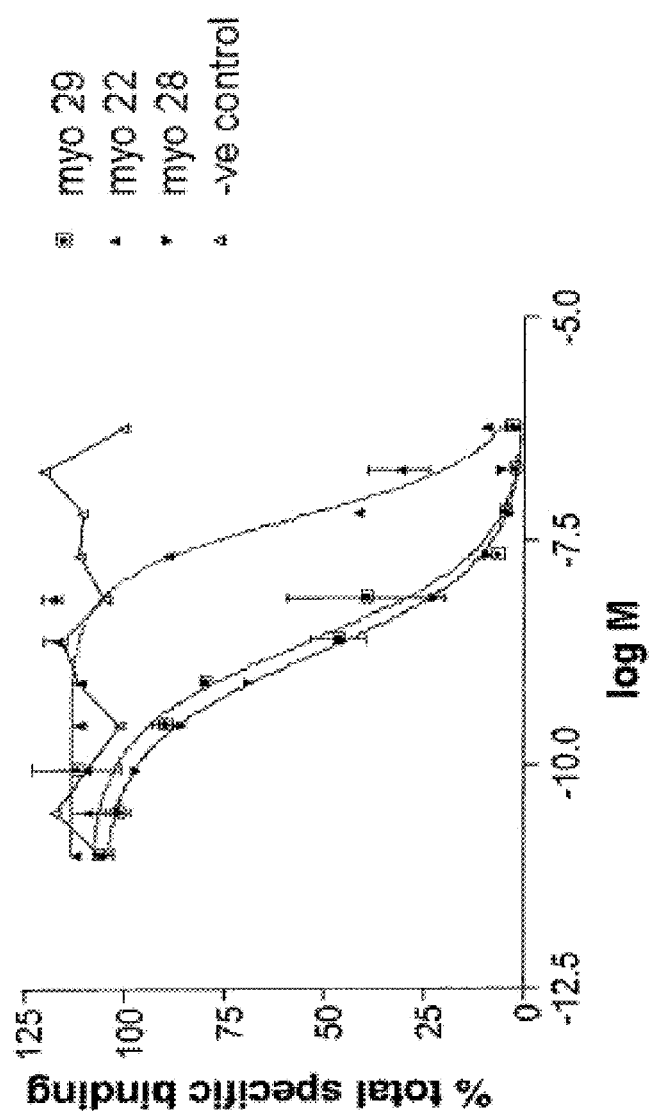
FIG. 2 shows inhibition of GDF-8 binding to the ActRIIB receptor by scFv fragments of the invention. As illustrated, the $IC_{50}$ for scFv's of Myo29, Myo28, and Myo22 are 2.4 nM, 1.7 nM, and 60 nM, respectively.

Purified scFv from positive clones identified from the receptor inhibition screen was tested in the inhibition assay as above. A titration of scFv concentrations was used in order to establish clone potency as measured by $IC_{50}$ values in the assay. The results of the experiments are shown in FIG. 2. As determined in these assays, $IC_{50}$ for scFv's of Myo29, Myo28, and Myo22 are 2.4 nM, 1.7 nM, and 60 nM, respectively. Therefore, these antibodies are potent inhibitors of GDF-8 activity.

Example 7

Specificity Characterization by Phage ELISA

To determine the specificity of antibodies, a phage ELISA was performed for positive clones from the ActRIIB screen against GDF-8 and unrelated proteins. Individual *E. coli* colonies containing phagemid were inoculated into 96 well plates containing 100 µl 2TYAG medium per well. M13K07 helper phage was added to a multiplicity of infection (moi) of 10 to exponentially growing culture and the plates incubated a further 1 hour at 37° C. Plates were centrifuged in a benchtop centrifuge at 2000 rpm for 10 minutes. The supernatant was removed and cell pellets were resuspended in 100 µl 2TYAK and incubated at 30° C. overnight with shaking. The next day, plates were centrifuged at 2000 rpm for 10 minutes and 100 µl phage-containing supernatant from each well transferred to a fresh 96 well plate. Phage samples were blocked in a final concentration of 3% MPBS for 1 hour at room temperature, prior to ELISA.

GDF-8 or irrelevant protein was coated overnight at 4° C. onto 96-well microtiter plates at 1 µg/ml. After coating, the solutions were removed from the wells, and the plates blocked for 1 hour at room temperature in 3% MPBS. Plates were rinsed with PBS then 50 µl of pre-blocked phage added to each well. The plates were incubated at room temperature for 1 hour and then washed with 3 changes of PBST followed by 3 changes of PBS. To each well, 50 µl of a 1:5000 dilution of anti-M13-HRP conjugate (Pharmacia) was added and the plates incubated at room temperature for 1 hour. Each plate was washed three times with PBST then 3 times with PBS. Fifty microliters of TMB substrate was added to each well and incubated until color development. The reaction was stopped by the addition of 25 µl of 0.5 M $H_2SO_4$. The signal generated was measured by reading the absorbance at 450 nm using a microtiter plate reader. Specific binding to GDF-8 was confirmed.

Example 8

Sequencing of scFv, Conversion to $IgG_1$ and Germlining

Neutralizing scFv *E. coli* clones were streaked out onto 2TYAG plates and incubated overnight at 30° C. Triplicate colonies from these plates were sequenced using pCANTAB6 vector sequence oligos to amplify the $V_H$ and $V_L$ regions from the scFv clone. DNA sequences of the scFv fragments used for making Myo29, Myo28, and Myo22 IgG's are represented by SEQ ID NO:13, SEQ ID NO:7, and SEQ ID NO:1, respectively.

Heavy and light chain V regions from scFv clones were amplified using PCR and clone-specific primers. PCR products were digested with appropriate restriction enzymes and subcloned into vectors containing human $IgG_1$ heavy chain constant domain (for $V_H$ domains) or vectors containing human lambda light chain constant domain as appropriate (for $V_L$ domains). Correct insertion of V region domains into plasmids was verified by sequencing of plasmid DNA from individual *E. coli* colonies. Plasmids were prepared from *E. coli* cultures by standard techniques and heavy and light chain constructs co-transfected into COS cells using standard techniques. Secreted IgG was purified using Protein A Sepharose (Pharmacia, Peapack, N.J.) and buffer exchanged into PBS.

Sequence data for the scFv clones was used to identify the nearest germline sequence for the heavy and light chain of each clone. Appropriate mutations were made using standard site directed mutagenesis techniques with the appropriate mutagenic primers. Mutation of scFv sequences was confirmed by sequence analysis. Germlined scFv and $V_H$ and $V_L$ domain sequences for Myo28 and Myo29 are set forth in SEQ ID NO:19 and SEQ ID NO:25, respectively.

Example 9

Biological Activity of Antibodies

Figure 3A:
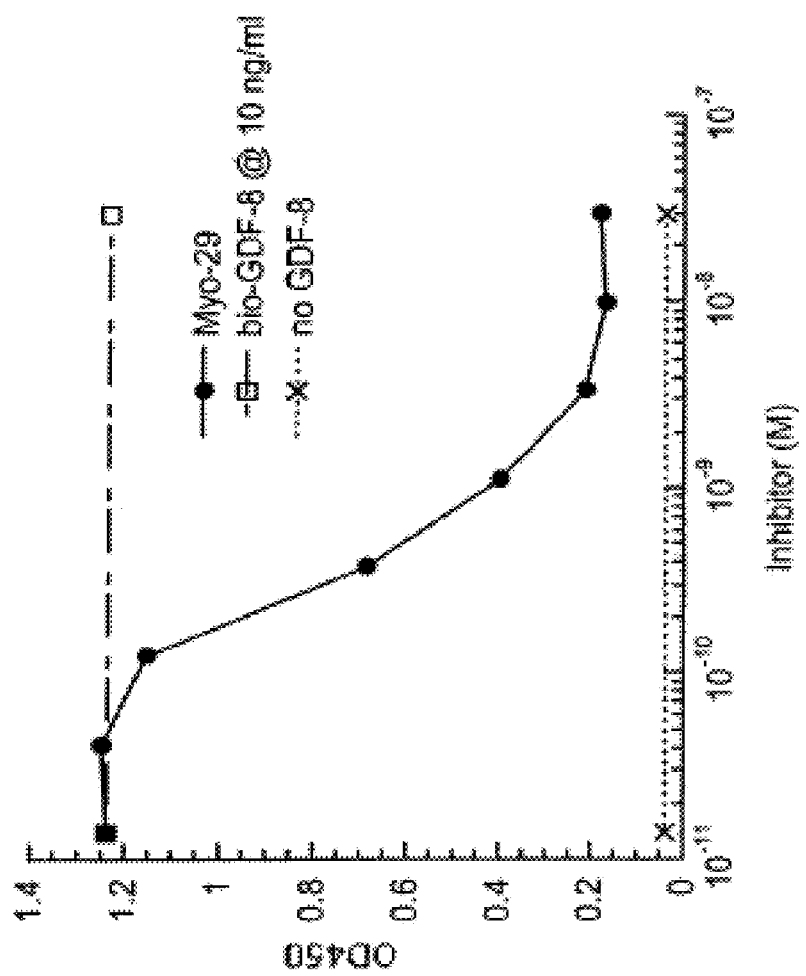
FIGS. 3A and 3B show that preincubation of Myo29 with biotinylated GDF-8 or BMP-11 at 10 ng/ml inhibits GDF-8 or BMP-11 binding to ActRIIB in the ActRIIB binding assay with an $IC_{50}$ of 0.2-0.4 nM.
Figure 3B:
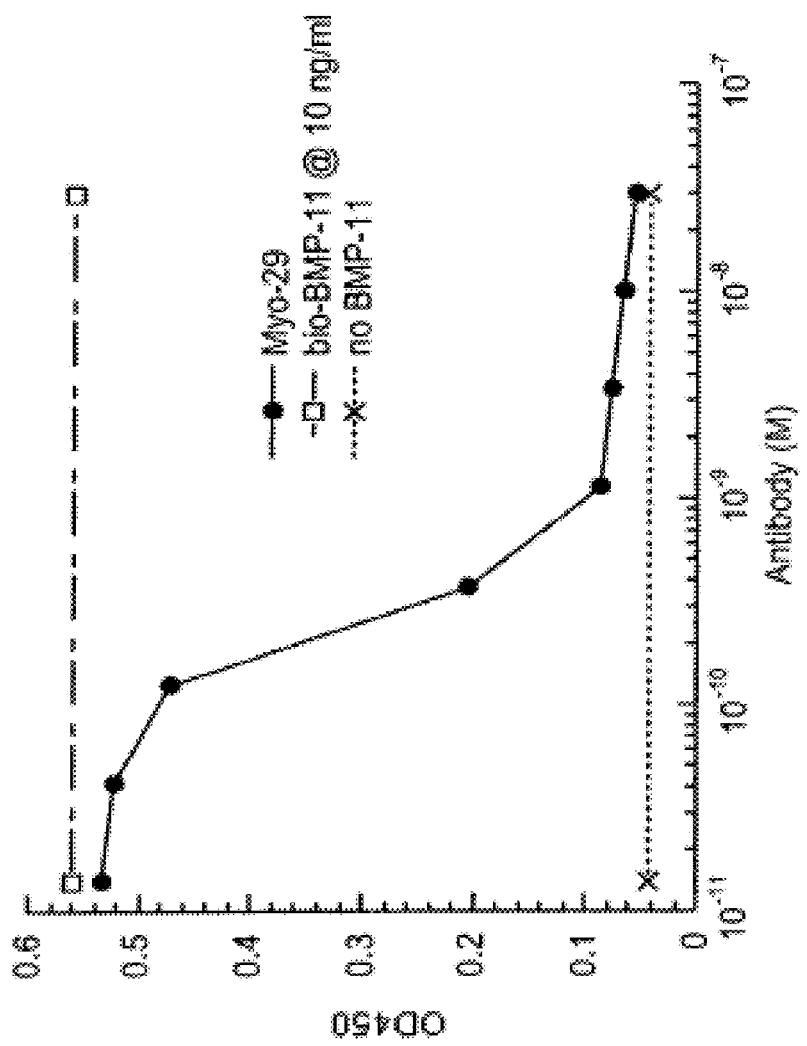

FIG. 3A shows that preincubation of Myo29 with biotinylated GDF-8 at 10 ng/ml inhibited GDF-8 binding to ActRIIB in the ActRIIB binding assay, as described in Example 3, with an $IC_{50}$ of 0.2-0.4 nM. Similarly in FIG. 3B, Myo29 inhibited biotinylated BMP-11 binding to ActRIIB with the same $IC_{50}$.

Figure 4B:
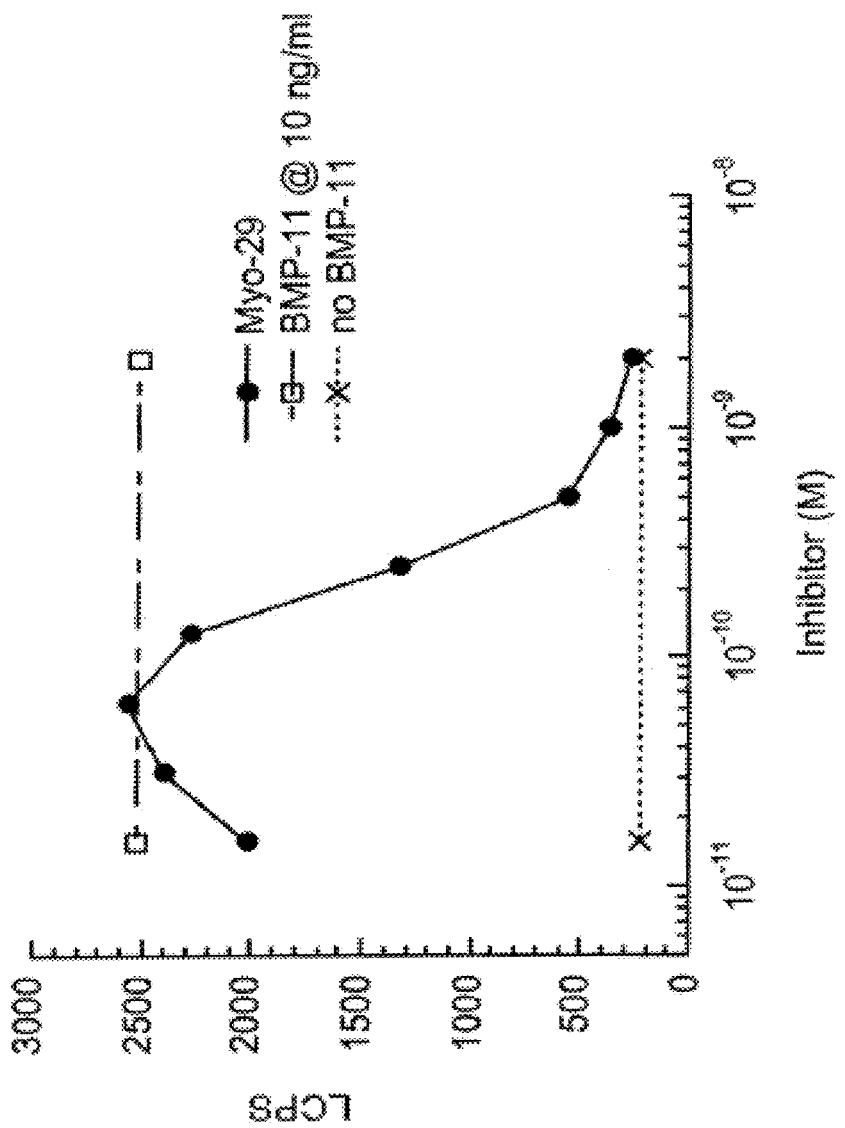
FIGS. 4B and 4C depict results of pGL3(CAGA)$_{12}$ reporter gene assays, in which Myo29 was tested.
Figure 4C:
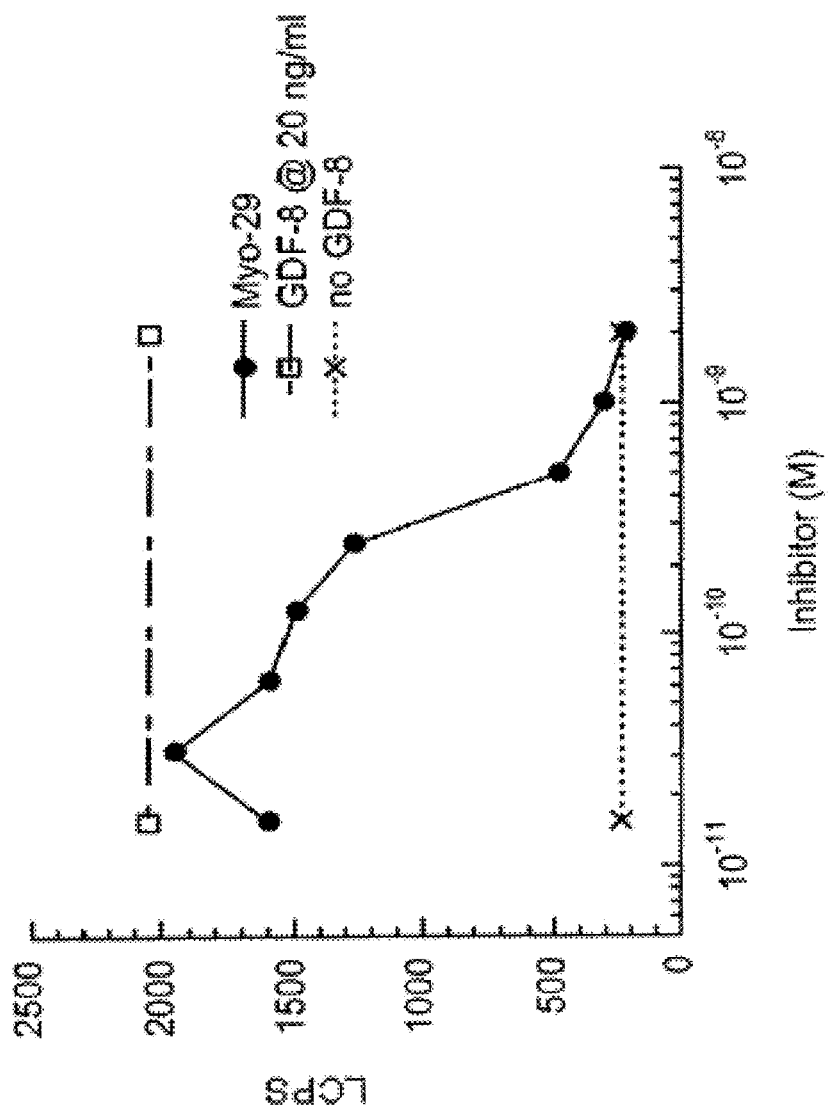

Myo29 also blocked GDF-8 activity in an in vitro bioassay. By way of example, when GDF-8 was preincubated with Myo29 for 1 hour at room temperature, the biological activity of GDF-8 was reduced as determined in RGA assays performed essentially as described in Example 2. FIG. 4C shows induction of pGL3(CAGA)$_{12}$ reporter activity at the $ED_{50}$ for GDF-8, 20 ng/ml, in the presence of Myo29. Myo29 reduced the GDF-8 induction in a dose-responsive manner, with an $IC_{50}$ of 15-30 ng/ml (0.1-0.2 nM). Myo29 also inhibited the biological activity of BMP-11 to the same extent (FIG. 4B). In contrast, the activity of activin in this assay was not affected by Myo29 (FIG. 4D), presumably due to the relatively low homology between GDF-8 and activin, as compared to GDF-8 and BMP-11.

Myo22 and Myo28 were also tested in the RGA and ActRIIB binding assays. Both antibodies block GDF-8 and BMP-11 activity. The $IC_{50}$ for Myo28, for example, is 0.2-0.35 nM.

Example 10

Mapping of Epitopes for Myo22, Myo28, and Myo29

In order to map the exact epitope of the antibodies, 48 overlapping 13-residue peptides representing the entire sequence of mature GDF-8 set forth in SEQ ID NO:49 were synthesized directly on cellulose paper using the spot synthesis technique (Molina et al. (1996) Peptide Research, 9:151-155; Frank et al. (1992) Tetrahedron, 48: 9217-9232). The overlap of the peptides was 11 amino acids. In this array, cysteine residues were replaced with serine in order to reduce the chemical complications that are caused by the presence of cysteines. Cellulose membranes modified with polyethylene glycol and Fmoc-protected amino acids were purchased from Abimed (Lagenfeld, Germany). The array was defined on the membrane by coupling a β-alanine spacer and peptides were synthesized using standard DIC (diisopropylcarbodiimide)/ HOBt (hydroxybenzotriazole) coupling chemistry as described previously (Molina et al. (1996) Peptide Research, 9: 151-155; Frank et al. (1992) Tetrahedron, 48: 9217-9232).

Figure 5:
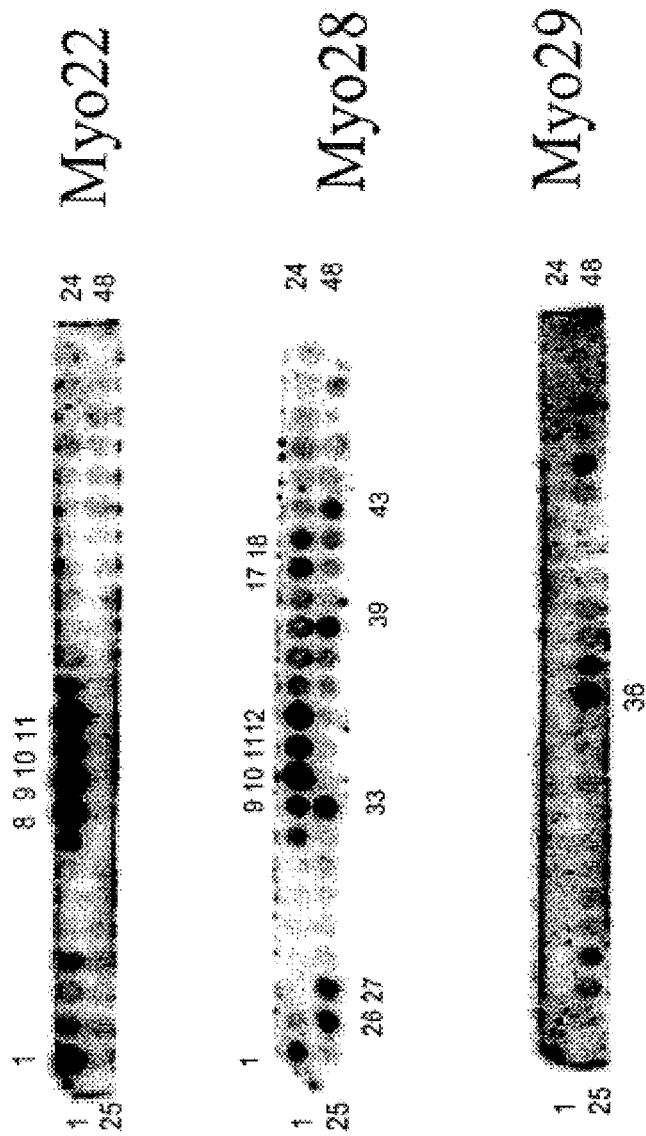
FIG. 5 shows results of epitope mapping for Myo22, Myo28, and Myo29. The epitope for Myo29 was mapped from amino acid 72 to amino acid 88 of mature GDF-8; for Myo22, from amino acid 1 to amino acid 44; for Myo28, from amino acids 1 to amino acid 98.

Activated amino acids were spotted using an Abimed ASP 222 robot. Washing and deprotection steps were done manually and the peptides were N-terminally acetylated after the final synthesis cycle. Following peptide synthesis, the membrane was washed in methanol for 10 minutes and in blocker (TBST (Tris-buffered saline with 0.1% (v/v) Tween™ 20) and 1% (w/v) casein) for 10 minutes. The membrane was then incubated with 2.5 µg/ml of an anti-GDF-8 antibody in blocker for 1 hour with gentle shaking. After washing with blocker 3 times for 10 minutes, the membrane was incubated with HRP-labeled secondary antibody (0.25 µg/ml in blocker) for 30 minutes. The membrane was then washed three times for 10 minutes each with blocker and 2 times for 10 minutes each with TBST. Bound antibody was visualized using SuperSignal™ West reagent (Pierce) and a digital camera (Alphananotech Fluoromager). Results are shown in FIG. 5. In particular, as seen from FIG. 5, the epitope for Myo29 was mapped between amino acids 72 and 88 of mature GDF-8. Myo22, on the other hand, recognizes an epitope within the first 44 N-terminal amino acids in the sequence of mature GDF-8 (amino acids 1 through 44 of SEQ ID NO:49). Finally, the epitope for Myo28 comprises residues located within the first 98 N-terminal amino acids of mature GDF-8.

Figure 6:
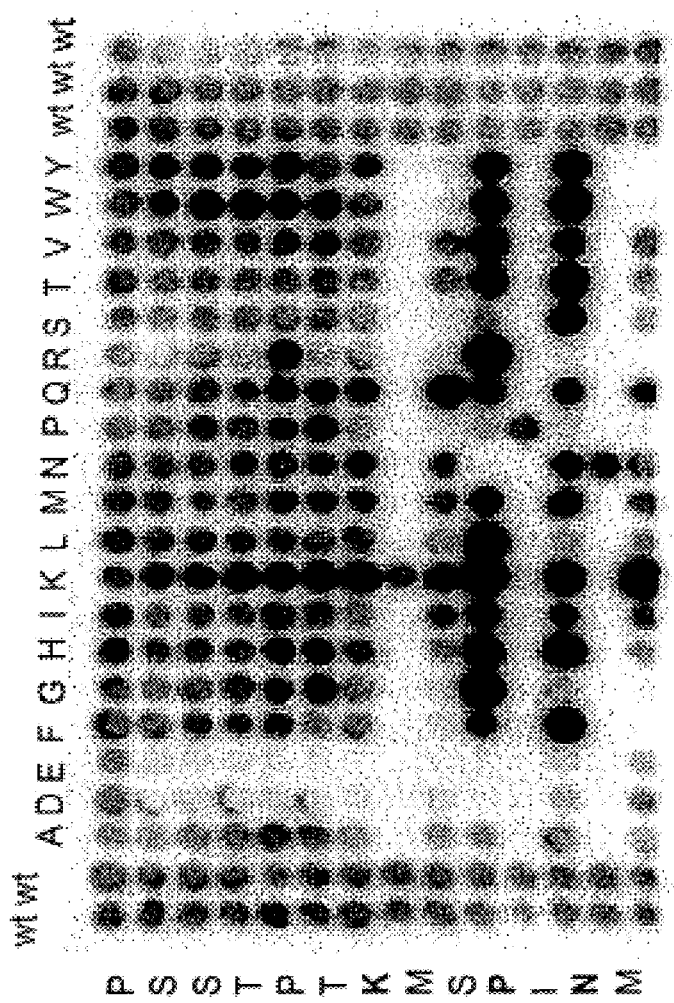
FIG. 6 demonstrates results of a substitution analysis of the Myo29 epitope. Residues Lys-78, Pro-81, and Asn-83 in mature GDF-8 appear to be important for Myo29 binding to GDF-8.

In order to further characterize the Myo29 epitope, deletion and substitution analyses were performed using spot synthesis. In the substitution analysis, each residue of this peptide was individually replaced with each of the 20 natural amino acids except cysteine. Synthesis and binding assays were performed as described above. The results are shown in FIG. 6, wherein the first row, first two columns and last three columns represent wild-type peptide controls. The results demonstrate that when Lys-78, Pro-81, and Asn-83 are each individually mutated to another amino acid, the binding affinity of Myo29 to the peptide is significantly reduced. Therefore, Myo29 recognizes a sequence comprising Lys-Xaa1-Xaa2-Pro-Xaa3-Asn (SEQ ID NO:54), wherein Xaa1, Xaa2, and Xaa3 each is either any amino acid, or Xaa1=Met, Xaa2=Ser, and Xaa3=Ile, independently of each other.

Example 11

Immunoprecipitation of GDF-8

Figure 7:
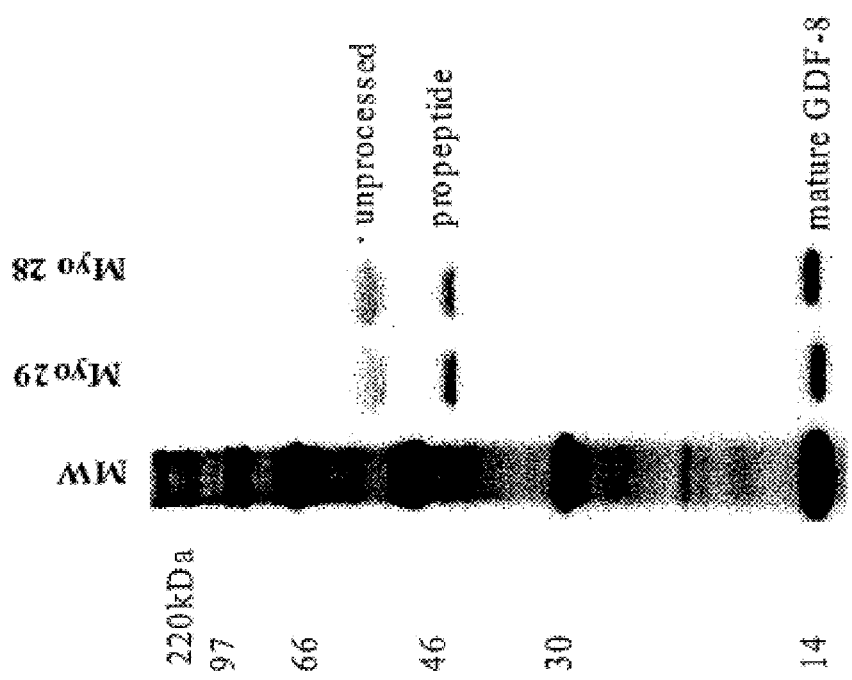
FIG. 7 depicts results of an immunoprecipitation experiment performed with Myo29 and Myo28. Conditioned medium from CHO cells expressing GDF-8, which were radiolabeled with $^{35}$S-methionine/cysteine, was subjected to immunoprecipitation with Myo29 or Myo28. The immunoprecipitates were then analyzed by SDS-PAGE under reducing conditions. Bands on the gel are identified as mature GDF-8, GDF-8 propeptide, and unprocessed GDF-8.

In order to evaluate the binding of Myo29 and Myo28 to mature GDF-8 and GDF-8 complexes, an immunoprecipitation study was conducted. CHO cells expressing GDF-8 were labeled with $^{35}$S-methionine and $^{35}$S-cysteine. 100 µl conditioned media from these cells, containing GDF-8 protein (mature GDF-8 and latent complex) was incubated with 20 µg/ml Myo29 or Myo28 for 1 hour at 4° C. Protein A-Sepharose™ was added and incubated overnight at 4° C. The immunoprecipitate was collected, resuspended in reducing sample buffer and analyzed by SDS-PAGE. The gel was fixed, enhanced with autoradiography enhancer solution, dried, and the autorad was developed. FIG. 7 shows that both Myo29 and Myo28 can immunoprecipitate mature GDF-8, the GDF-8 latent complex and unprocessed GDF-8. Both antibodies bind to GDF-8 dimer under non-reducing conditions as determined by Western blotting.

Example 12

Pharmacokinetics

Figure 8:
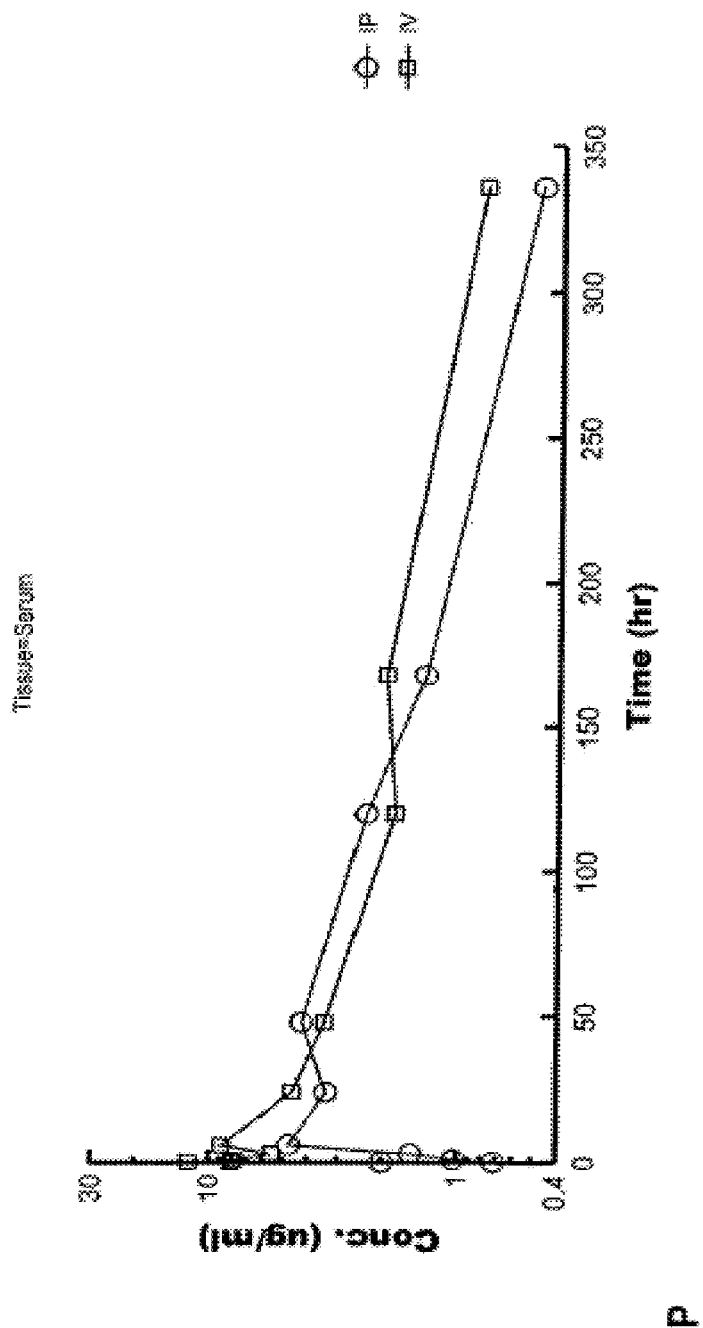
FIG. 8 depicts results of a pharmacokinetic study in which C57B6/SCID mice received a dose of 1 mg/kg as a single intravenous (IV) or intraperitoneal (IP) administration of Myo29. Myo29 shows prolonged terminal half-life of around one week and low clearance around 1 ml/hr/kg. The fraction absorbed following IP injection is about 77%.

The pharmacokinetics (PK) of Myo29 was evaluated in C57B6/SCID mice at a dose of 1 mg/kg after a single intravenous (IV) or intraperitoneal (IP) administration. The animals received a mixture of unlabeled and $^{125}$I-labeled Myo29 at the dose listed above and serum concentrations were determined based on $^{125}$I radioactivity in the serum and the specific activity of the injected dose. FIG. 8 shows a plot of serum concentration versus time for Myo29 administered either IV or IP.

Myo29 showed a prolonged terminal half-life of around one week and low clearance around 1 ml/hr/kg. Initial volume of distribution was about 83 ml/kg. Apparent volume of distribution was about 227 ml/kg. Myo29 reached a peak concentration at about 6 hrs post injection. Fraction absorbed following IP injection was about 77%.

Example 13

In Vivo Effect of Myo29 on Muscle Mass and Strength

In order to determine whether Myo29 blocks GDF-8 activity in vivo, Myo29 was tested in adult SCID mice. SCID mice suffer from a severe combined immune deficiency, and therefore do not generate an immunological reaction following injections of human antibodies such as Myo29. Muscle mass was used as an indicator for GDF-8 activity in mice treated with Myo29.

Figure 9:
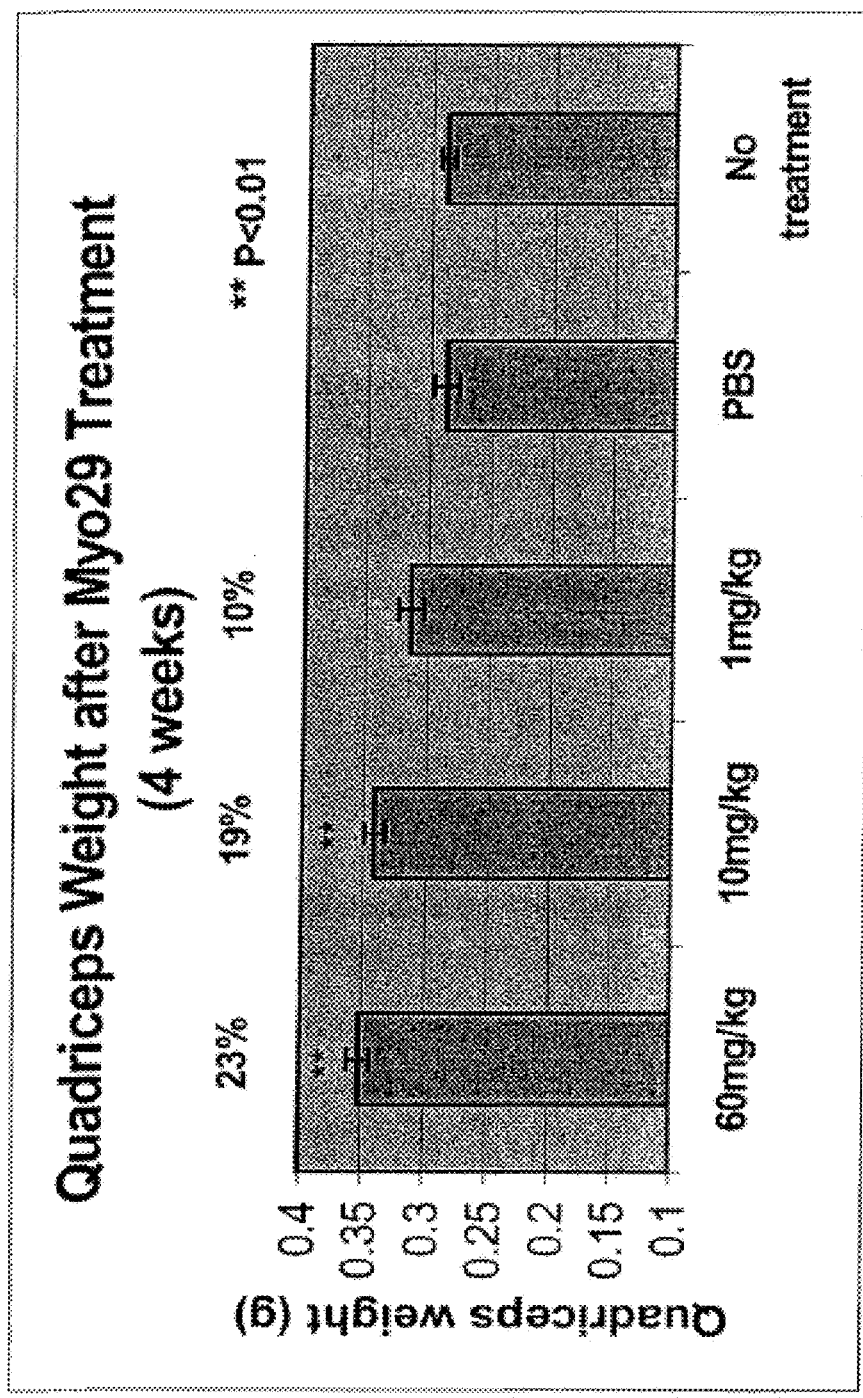
FIG. 9 shows comparisons of quadriceps mass in male C57B6/SCID mice treated weekly with various doses of Myo29 (60, 10, and 1 mg/kg), or vehicle (PBS). Treatment with Myo29, at the 10 and 60 mg/kg dose levels for four weeks results in a statistically significant increase in muscle mass of 19% and 23%, respectively.

Male C57B6 SCID eight weeks old mice were weighed and evenly distributed with respect to body weight into groups of eight. Myo29 in PBS buffer was injected into the mice intraperitoneally at various doses (60, 10, and 1 mg/kg) weekly. A double dose was given the first week. Vehicle (PBS)-treated or untreated mice were used as controls. The treatments continued for four weeks. Muscle mass was assessed by dissecting and weighing the gastrocnemius and quadriceps following treatment. After four weeks of treatment, muscle mass was increased in all groups treated with Myo29, ranging from 10% to 23%, with groups treated with higher doses reaching significant levels (FIG. 9, p<0.01).

Figure 10A:
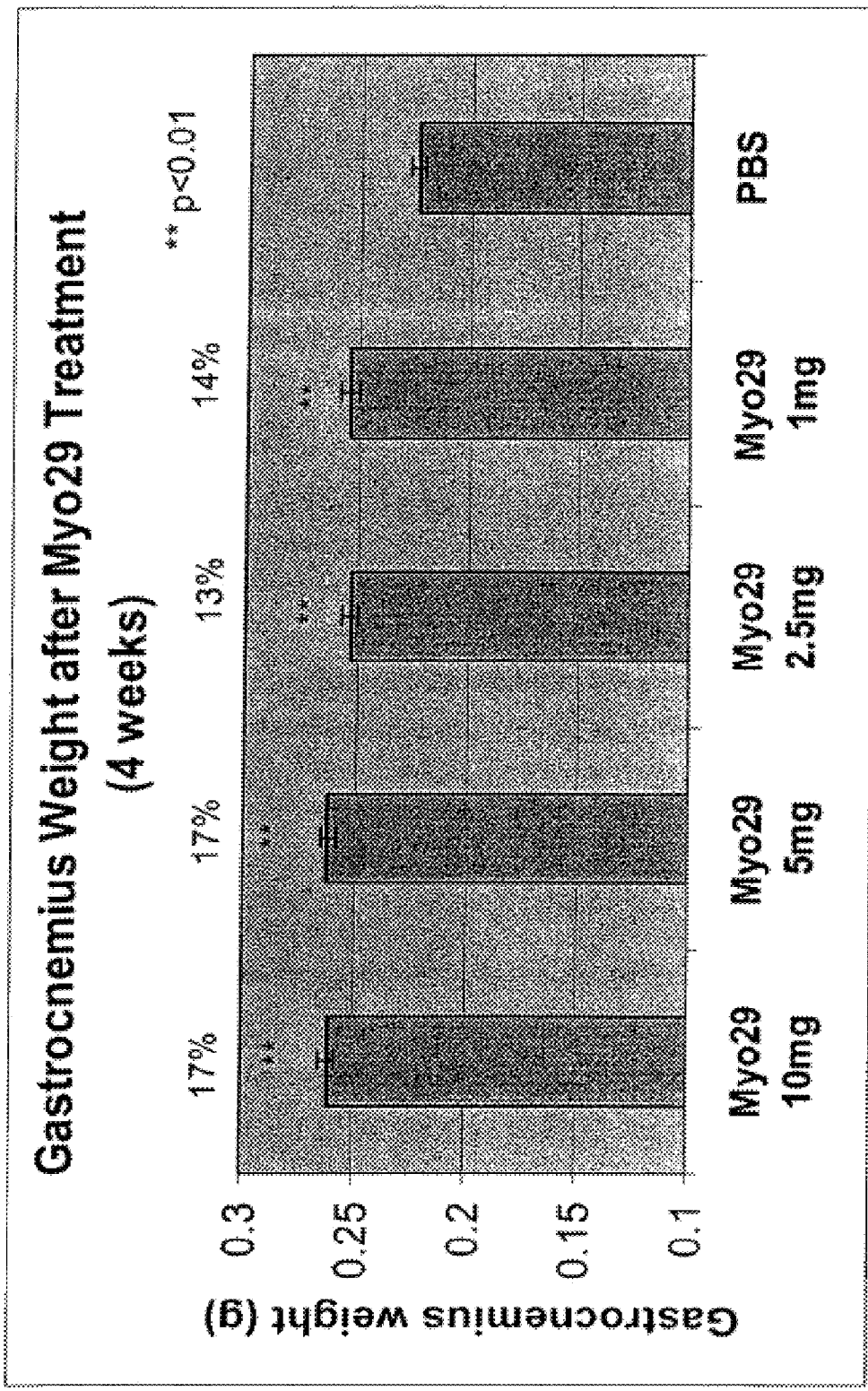
FIGS. 10A and 10B show gastrocnemius and quadriceps mass in female CB17 SCID mice treated weekly with various doses of Myo29 (10, 5, 2.5, and 1 mg/kg) or PBS for four weeks. Muscle mass is increased by 10 to 20% in mice treated with Myo29 as compared to the vehicle control.
Figure 10B:
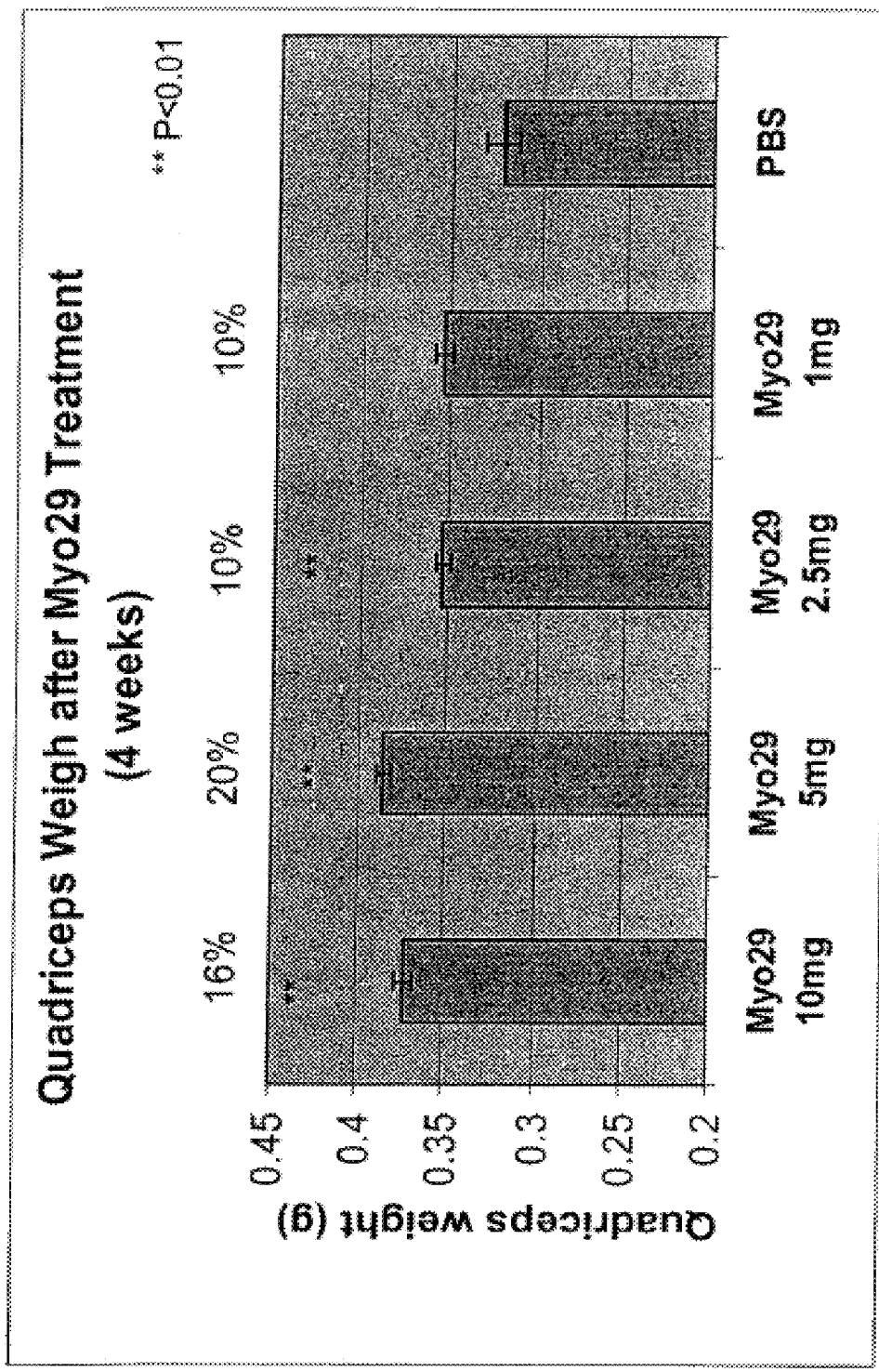
Figure 11A:
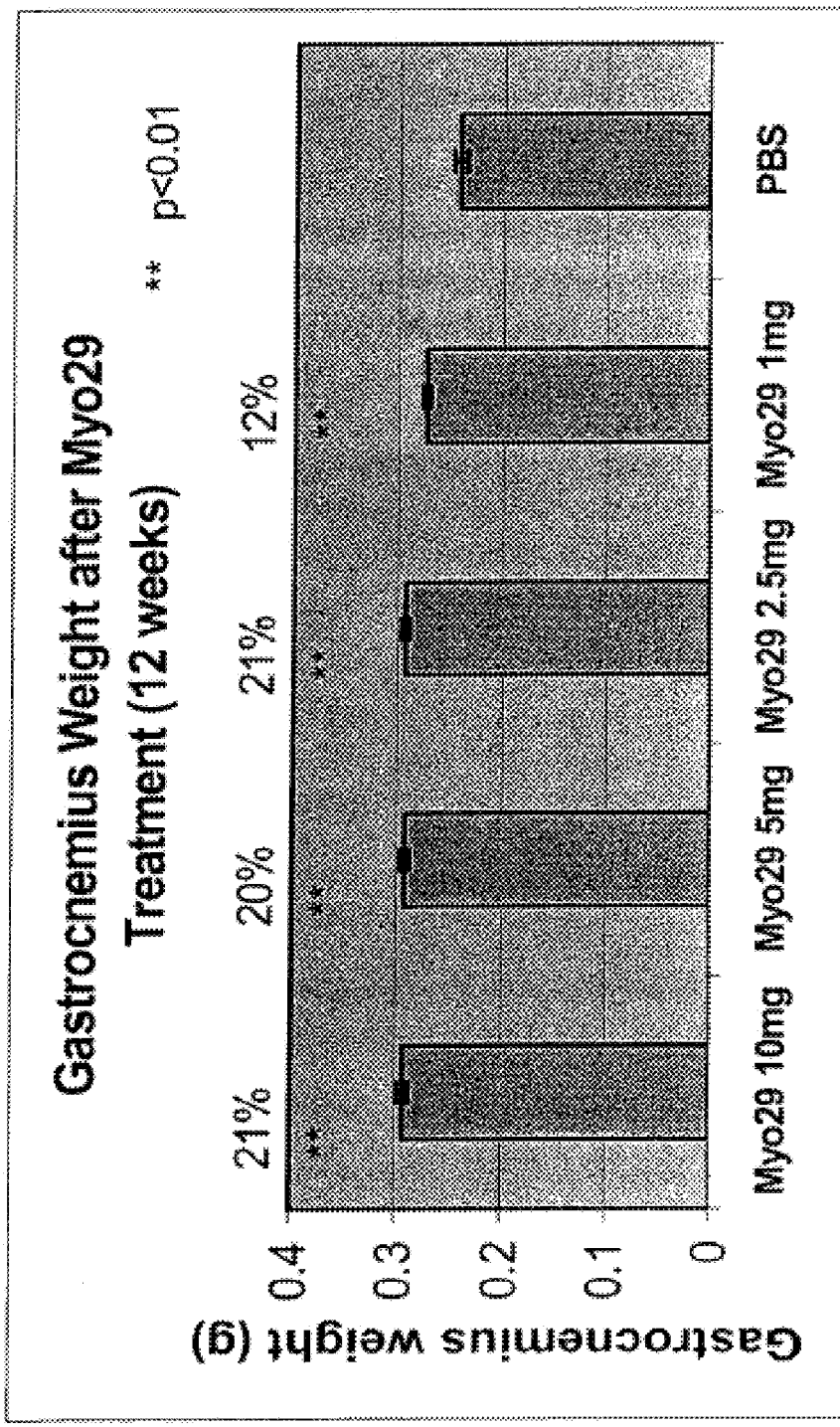
FIGS. 11A and 11B demonstrate respectively gastrocnemius and quadriceps muscle mass in female CB17 SCID mice treated weekly with various doses of Myo29 (10, 5, 2.5, and 1 mg/kg) or PBS for twelve weeks. Mice treated with Myo29 show increases in muscle mass ranging from 12 to 28%.
Figure 11B:
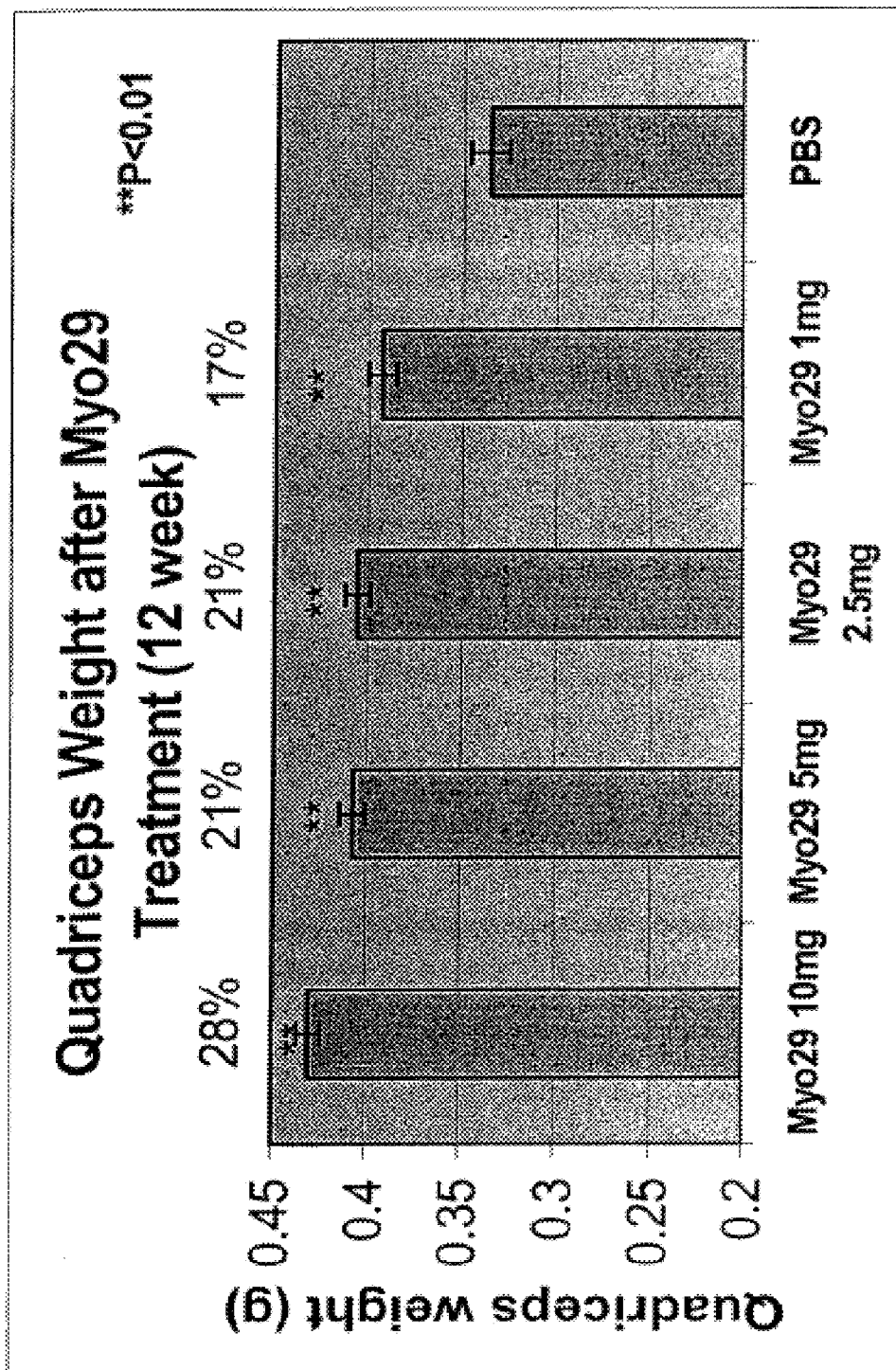

In another experiment, female CB17 SCID mice were treated with Myo29 weekly at various doses (10, 5, 2.5, and 1 mg/kg) for 4 or 12 weeks. Again, treatments with Myo29 for 4 weeks resulted in an increase in gastrocnemius and quadriceps weight ranging from 10% to 20% (FIGS. 10A and 10B). Longer treatment (12 weeks) resulted in greater increases in muscle mass (12% to 28%) with all groups treated with Myo29 reaching statistically significant levels (FIGS. 11A and 11B).

Figure 12:
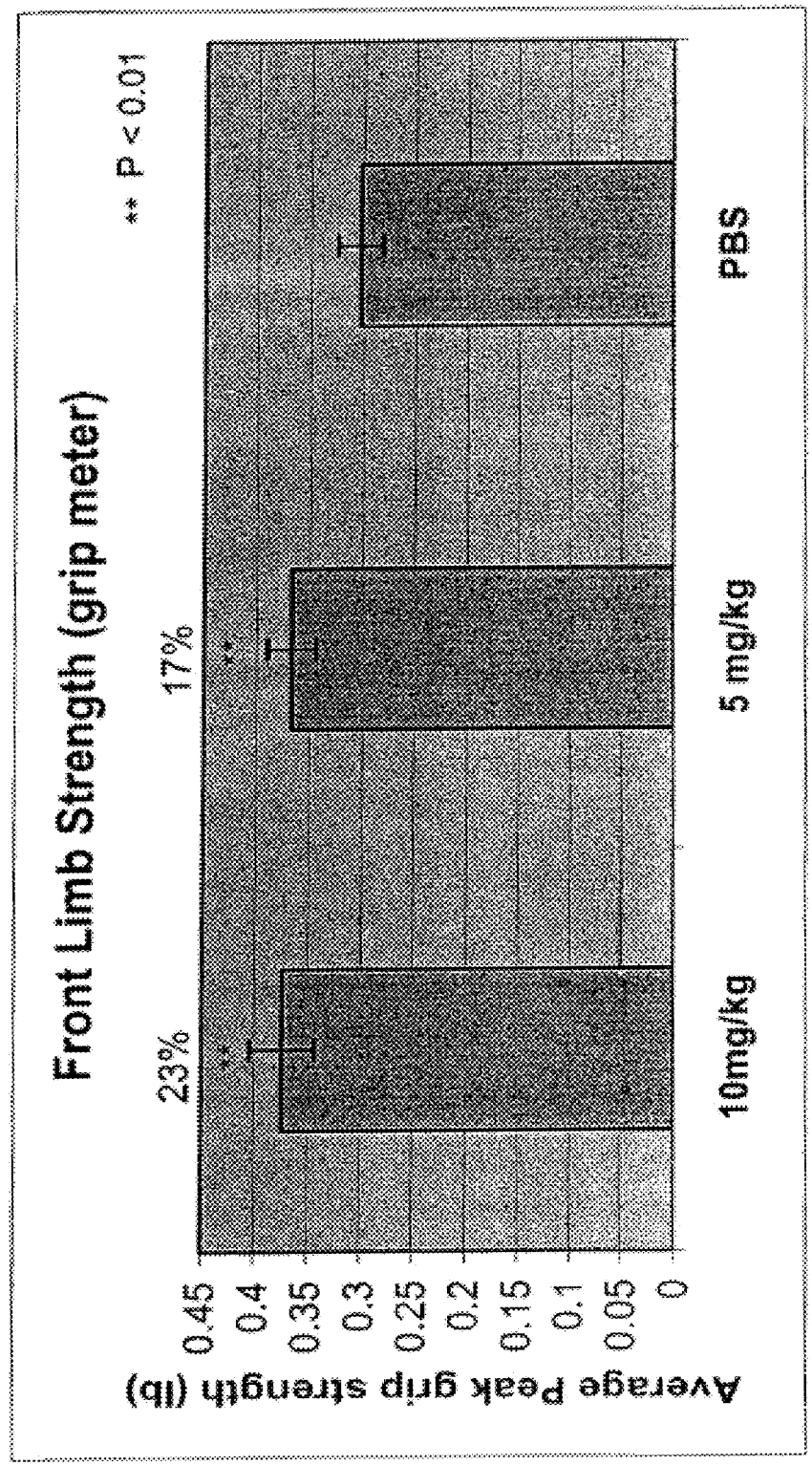
FIG. 12 shows the front limb muscle strength, as measured by a grip strength meter, in female CB17 SCID mice treated weekly with Myo29 (10 and 5 mg/kg) or PBS for twelve weeks. Front limb strength is increased by 17% and 23% in mice treated with Myo29 at 5 mg/kg and 10 mg/kg, respectively.

In order to determine whether increased muscle mass leads to stronger muscles, muscle strength of front limb was measured with a grip strength test meter (model 1027 csx, Columbus Instruments, Columbus, Ohio). After 12 weeks of treatment, the front limb strength was 17% and 23% higher in mice treated with 5 mg/kg or 10 mg/kg of Myo29 respectively as compared to the vehicle control (p<0.01, FIG. 12). The results of this study demonstrate that Myo29 inhibits GDF-8 activity in vivo resulting in significant increases in muscle mass and muscle strength.

Example 14

Treatment of Metabolic Disorders

Inhibitors of GDF-8, such as, for example inhibitory antibodies, are useful for treatment of metabolic disorders such as type 2 diabetes, impaired glucose tolerance, metabolic syndrome (e.g., syndrome X), insulin resistance induced by trauma (e.g., burns or nitrogen imbalance), and adipose tissue disorders (e.g., obesity). The anti-GDF-8 antibodies of the invention are used to treat a subject at disease onset or having an established metabolic disease.

Efficacy of anti-GDF-8 antibodies for treatment of metabolic disorders, e.g., type 2 diabetes and/or obesity, is confirmed using well established murine models of obesity, insulin resistance and type 2 diabetes, including ob/ob, db/db, and strains carrying the lethal yellow mutation. Insulin resistance can also be induced by high fat or high caloric feeding of certain strains of mice, including C57BL/6J. Similarly to humans, these rodents develop insulin resistance, hyperinsulinemia, dyslipidemia, and deterioration of glucose homeostasis resulting in hyperglycemia. Outcome assessments are based on serum measurements of glucose, insulin and lipids. Measures of improved insulin sensitivity can be determined by insulin tolerance tests and glucose tolerance tests. More sensitive techniques would include the use of euglycemic-hyperinsulinemic clamps for assessing improvements is glycemic control and insulin sensitivity. In addition, the clamp techniques would allow a quantitative assessment of the role of the major glucose disposing tissues, (muscle, adipose, and liver), in improved glycemic control.

In one study, treatment with an anti-GDF-8 antibody such as Myo29 (IP injection) or vehicle is conducted for one week to six months. The treatment protocol could vary, with testing of different doses and treatment regimens (e.g., daily, weekly, or bi-weekly injections). It is anticipated that mice treated with the anti-GDF-8 antibody would have greater glucose uptake, increased glycolysis and glycogen synthesis, lower free fatty acids and triglycerides in the serum as compared to mice receiving placebo treatment.

The inhibitory antibodies against GDF-8 are also used to prevent and/or to reduce severity and/or the symptoms of the disease. It is anticipated that the anti-GDF-8 antibodies would be administered as a subcutaneous injection as frequently as once per day and as infrequently as once per month. Treatment duration could range from one month to several years.

To test the clinical efficacy of anti-GDF-8 in humans, subjects suffering from or at risk for type 2 diabetes are identified and randomized to a treatment group. Treatment groups include a placebo group and one to three groups receiving antibody (different doses). Individuals are followed prospectively for one month to three years to assess changes in glucose metabolism. It is anticipated that individuals receiving treatment would exhibit an improvement.

The antibodies are administered as the sole active compound or in combination with another compound or composition. When administered as the sole active compound or in combination with another compound or composition, the dosage is preferably from approximately 1 µg/kg to 20 mg/kg, depending on the severity of the symptoms and the progression of the disease. The appropriate effective dose is selected by a treating clinician from the following ranges: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg to 1 mg/kg, and 500 µg/kg to 1 mg/kg. Exemplary treatment regimens and outcomes are summarized in Table 3.

TABLE 3

Examples of Clinical Cases

| Patient No. | Status prior to treatment | Treatment Regimen | Outcome |
| --- | --- | --- | --- |
| Patient 1 | No clinical signs, family history of type 2 diabetes | 0.01-1 mg/kg every 4 weeks for 48 weeks | Prevention of type 2 diabetes |
| Patient 2 | Mild clinical signs of syndrome X | 0.01-20 mg/kg weekly for 4 more weeks | Improved insulin tolerance and glucose metabolism, and lower blood pressure |
| Patient 3 | Advanced stage of type 2 diabetes | 0.01-20 mg/kg twice weekly for 6 or more weeks | Improvement of clinical signs, reduction in severity of symptoms and/or increase in muscle mass/body fat ratio |
| Patient 4 | Severe insulin resistance and/obesity | 0.01-20 mg/kg daily for 6 or more weeks | Improvement of clinical signs, reduction in severity of symptoms and/or decrease in body fat |

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

We claimed:

1. An isolated antibody or fragment thereof that specifically binds GDF-8, comprising:
   an antibody variable heavy (VH) domain comprising the first, second and third complementarity determining regions (CDR) from the VH domain defined by the amino acid sequence of SEQ ID NO:10 or SEQ ID NO:22; and
   an antibody variable light (VL) domain comprising the first, second and third complementarity determining regions (CDR) from the VL domain defined by the amino acid sequence of SEQ ID NO:12 or SEQ ID NO:24.

2. The antibody or fragment of claim 1, wherein VH CDR1 comprises SEQ ID NO:37, VH CDR2 comprises SEQ ID NO:38, VH CDR3 comprises SEQ ID NO:39, VL CDR1 comprises SEQ ID NO:40, VL CDR2 comprises SEQ ID NO:41, and VL CDR3 comprises SEQ ID NO:42.

3. The antibody or fragment of claim 1, wherein said VH region comprises the amino acid sequence of SEQ ID NO:22 and said VL region comprises the amino acid sequence of SEQ ID NO:24.

4. The antibody or fragment of claim 1, further comprising an antibody heavy chain constant region from a human immunoglobulin subtype selected from the group consisting IgG1, IgG2, IgG3, IgG4, IgA1, IgA2, IgD, IgE, and IgM.

5. The antibody or fragment of claim 4, wherein said heavy chain constant region is modified to alter a constant region effector function.

6. The antibody or fragment of claim 5, wherein said constant region effector function is Fc receptor binding.

7. The antibody or fragment of claim 1, further comprising a kappa or lambda human antibody light chain constant region.

8. An isolated antibody that specifically binds GDF-8, comprising:
   two heavy chains, each comprising the VH region of the amino acid sequence of SEQ ID NO:22 and the heavy chain constant region from human IgG1; and
   two light chains, each comprising the VL region of the amino acid sequence of SEQ ID NO:24 and the light chain constant region of the amino acid sequence of SEQ ID NO:51.

9. The antibody of claim 8, wherein the human IgG1 antibody heavy chain constant region is the amino acid sequence of SEQ ID NO:53 modified at least at residue 117 or 120 to alter an Fc region effector function.

10. The antibody or fragment of claim 1, wherein said antibody or fragment is partially or fully humanized.

11. The antibody or fragment of claim 1, wherein said antibody or fragment is neutralizing.

12. A pharmaceutical composition comprising the antibody or fragment of claim 1 and a pharmaceutically acceptable carrier.

* * * * *